United States Patent
Stemp et al.

[11] Patent Number: 6,046,210
[45] Date of Patent: Apr. 4, 2000

[54] TETRAHYDROISOQUINOLINE DERIVATIVES AS MODULATORS OF DOPAMINE $D_3$ RECEPTORS

[75] Inventors: Geoffrey Stemp, Bishop's Stortford; Amanda Johns, St Albans, both of United Kingdom

[73] Assignee: SmithKline Beecham p.l.c., Brentford Middlesex, United Kingdom

[21] Appl. No.: 09/180,156

[22] PCT Filed: May 6, 1997

[86] PCT No.: PCT/EP97/02434

§ 371 Date: Nov. 3, 1998

§ 102(e) Date: Nov. 3, 1998

[87] PCT Pub. No.: WO97/43262

PCT Pub. Date: Nov. 20, 1997

[30] Foreign Application Priority Data

May 11, 1996 [GB] United Kingdom .................. 9609888
Aug. 16, 1996 [GB] United Kingdom .................. 9617189
Aug. 5, 1997 [GB] United Kingdom .................. 9704490

[51] Int. Cl.[7] ..................... C07D 217/04; A61K 31/47
[52] U.S. Cl. ............................. 514/307; 546/146
[58] Field of Search .................. 546/146; 514/307

[56] References Cited

U.S. PATENT DOCUMENTS 5,294,621  3/1994  Russell .................................... 514/301

FOREIGN PATENT DOCUMENTS

WO 96/02246  2/1996  WIPO .

*Primary Examiner*—Zinna Northington Davis
*Attorney, Agent, or Firm*—Nora Stein-Fernandez; Janice E. Williams; Charles M. Kinzig

[57] ABSTRACT

This invention relates to compounds of formula (I):

Formula (I)

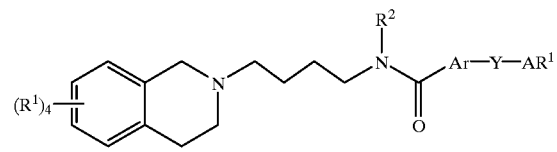

which are useful as modulators of $D_3$ receptors, in particular in the treatment of psychoses.

11 Claims, No Drawings

TETRAHYDROISOQUINOLINE DERIVATIVES AS MODULATORS OF DOPAMINE $D_3$ RECEPTORS

This application is a 371 of PCT/EP97/02434 filed May 6, 1997.

The present invention relates to novel tetrahydroisoquinoline derivatives, processes for their preparation, pharmaceutical compositions containing them and their use in therapy, as modulators of dopamine $D_3$ receptors, in particular as antipsychotic agents.

U.S. Pat. No. 5,294,621 describes tetrahydropyridine derivatives of the formula:

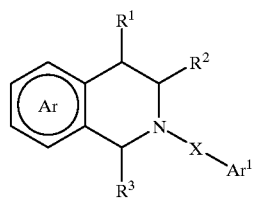

wherein

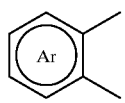

is an optionally substituted thienyl or optionally substituted phenyl ring; $R^1$, $R^2$ and $R^3$ are each inter alia hydrogen; X is inter alia $(CH_2)mNR^7CO$; m is 2–4; and $Ar^1$ is an optionally substituted heterocyclic ring or an optionally substituted phenyl ring. The compounds arm said to be useful as antiarrhythmic agents.

We have now found a class of tetrahydroisoquinoline derivatives which have affinity for dopamine receptors, in particular the $D_3$ receptor, and thus potential in the treatment of conditions wherein modulation of the $D_3$ receptor is beneficial, eg as antipsychotic agents.

In a first aspect the present invention provides compounds of formula (I):

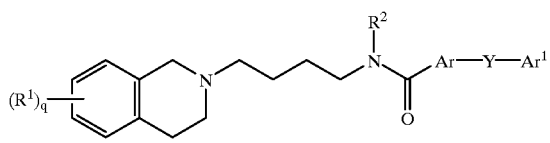

Formula (I)

wherein:
$R^1$ represents a substituent selected from: a hydrogen or halogen atom; a hydroxy, cyano, nitro, trifluoromethyl, trifluoromethoxy, trifluoromethanesulfonyloxy, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy, arylsulphonyl$C_{1-4}$alkyl, $C_{1-4}$alkylsulphonamido, $C_{1-4}$alkylamido, $C_{1-4}$alkylsulphonamido$C_{1-4}$alkyl, $C_{1-4}$alkylamido$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH_2)_p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group $Ar^2$—Z, wherein $Ar^2$ represents an optionally substituted phenyl ring or an optionally substituted 5- or 6-membered aromatic heterocyclic ring and Z represents a bond, O, S, or $CH_2$;

$R^2$ represents a hydrogen atom or a $C_{1-4}$alkyl group;

q is 1 or 2;

Ar and $Ar^1$ each independently represent an optionally substituted phenyl ring or an optionally substituted 5- or 6-membered aromatic heterocyclic ring; and Y represents a bond, —NHCO—, —CONH—, —$CH_2$—, or —$(CH_2)_mY^1(CH_2)_n$—, wherein $Y^1$ represents O, S, $SO_2$, or CO and m and n each represent zero or 1 such that the sum of m+n is zero or 1;

and salts thereof.

In the compounds of formula (I) above an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-pentyl, and the like.

When $R^1$ represents an aryl$C_{1-4}$alkoxy, arylsulphonyl, arylsulphonyloxy, arylsulphonyl$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group, the aryl moiety may be selected from an optionally substituted phenyl ring or an optionally substituted 5- or 6-membered heterocyclic ring. In the group $R^1$ an aryl moiety may be optionally substitued by one or more substituents selected from hydrogen, halogen, amino, cyano, $C_{1-4}$alkyl, $C_{1-4}$alkylamino, $C_{1-4}$dialkylamino, $C_{1-4}$alkylamido, $C_{1-4}$alkanoyl, or $R^5R^6$NCO where each of $R^5$ and $R^6$ independently represents a hydrogen atom or $C_{1-4}$alkyl group.

A halogen atom present in the compounds of formula (I) may be fluorine, chlorine, bromine or iodine.

When q is 2, the substituents $R^1$ may be the same or different. Preferably q represents 1.

An optionally substituted 5- or 6-membered heterocyclic aromatic ring, as defined for either of the groups Ar, $Ar^1$ or $Ar^2$ may contain from 1 to 4 heteroatoms selected from O, N or S. When the ring contains 2–4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl.

The rings Ar, $Ar^1$ or $Ar^2$ may each indepenendy be optionally substituted by one or more substituents selected from: a hydrogen or halogen atom, or a hydroxy, cyano, nitro, $C_{1-4}$alkyl, $C_{1-4}$alkoxy, $C_{1-4}$alkanoyl, $C_{1-4}$alkylsulphonyl, $C_{1-4}$alkylaminosulphonyl or $C_{1-4}$dialkylaminosulphonyl group.

Alternatively, $Ar^1$ may be optionally substituted by one or more substituents selected from: a 5- or 6-membered heterocyclic ring, as defined above, optionally substituted by a $C_{1-2}$alkyl group; a group —$CONR^7R^8$, $R^7R^8NSO2$—, or $R^7CON(R^8)$—wherein each of $R^7$ and $R^8$ independently represents a hydrogen atom or a $C_{1-4}$alkyl group, or $R^7R^8$ together form a $C_{3-6}$alkylene chain. Substituents positioned ortho to one another may be linked to form a 5- or 6-membered ring.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulphuric, nitric or phosphoric acid; and organic acids eg. succinic, maleic, acetic, fumaric, citric, tartaric, benzoic, p-toluenesulphonic, methanesulphonic or naphthalenesulphonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

Particular compounds according to the invention include:

7-Methoxy-N-(4-(4-phenylbenzoylamino)butyl)-1,2,3,4-tetrahydroisoquinoline;

7-Hydroxy-N-(4-(4-phenylbenzoylamino)butyl)-1,2,3,4-tetrahydroisoquinoline; 2-(4-(4-(4-Cyanophenyl)benzoylamino)butyl)-7-hydroxy-1,2,3,4-tetrahydroisoquinoline 2-(4-(4-(4-Acetylphenyl)benzoylamino)butyl)-7-hydroxy-1,2,3,4-tetrahydroisoquinoline N-(4-(4-Phenylbenzoylamino)butyl)-7-trifluoromethylsulfonyloxy-1,2,3,4-tetrahydmuisoquinoline;

7-Methylsulfonyloxy-N-(4-(4-phenylbenzoylamino)butyl)-1,2,3,4-tetrahydroisoquinoline;

2-(4-(4-(3-Cyanophenyl)benzoylamino)butyl)-7-methoxy-1,2,3,4-tetrahydroisoquinoline;

2-(4-(4-(4-Cyanophenyl)benzoylamino)butyl)-7-methoxy-1,2,3,4-tetrahydroisoquinoline;

2-(4-(4-(4-Acetylphenyl)benzoylamino)butyl)-7-methoxy-1,2,3,4-tetrahydroisoquinoline;

2-(4-(4-(3-Cyanophenyl)benzoylamino)butyl-7-hydroxy-1,2,3,4-tetrahydroisoquinoline;

2-(4-(4-(3-Cyanophenyl)benzoylamino)butyl)-7-trifluoromethylsulfonyloxy-1,2,3,4-tetrahydroisoquinoline;

2-(4-(4-(4-Cyanophenyl)benzoylamino)butyl)-7-trifluoromethylsulfonyloxy-1,2,3,4-tetrahydroisoquinoline;

2-(4-(4-(4-Acetylphenyl)benzoylamino)butyl)-7-trifluoromethylsulfonyloxy-1,2,3,4-tetrahydroisoquinoline;

2-(4-(4-(4-Methylsulfonylphenyl)benzoylamino)butyl)-7-trifluoromethylsulfonyloxy-1,2,3,4-tetrahydroisoquinoline;

2-(4-(4-Phenylbenzoylamino)butyl)-7-(2-thienyl)sulfonyloxy-1,2,3,4-tetrahydroisoquinoline;

7-(4-(3,5-Dimethyl)isoxazolyl)sulfonyloxy-2-(4-(4-phenylbenzoylamino)butyl)-1,2,3,4-tetrahydroisoquinoline;

7-Acetyl-2-(4-(4-phenylbenzoylamino)butyl)-1,2,3,4-tetrahydroisoquinoline;

7-Methoxy-2-(4-(4-(6-methyl)-3-pyridyl)benzoylamino)butyl-1,2,3,4-tetrahydroisoquinoline;

2-(4-(4-(3-Thienyl)benzoylamino)butyl)-7-trifluoromethylsulfonyloxy-1,2,3,4-tetrahydroisoquinoline;

2-(4-(4-(3-Aminocarbonyl)phenyl)benzoylamino)butyl-7-trifluoromethylsulfonyloxy-1,2,3,4-tetrahydroisoquinoline;

2-(4-(4-(3-Acetylphenyl)benzoylamino)butyl)-7-trifluoromethylsulfonyloxy-1,2,3,4-tetrahydroisoquinoline;

2-(4-(4-(3-Methylsulfonylphenyl)benzoylamino)butyl)-7-trifluoromethylsulfonyloxy-1,2,3,4-tetrahydroisoquinoline;

2-(4-(4-(1-Methyl-4-pyrazolyl)benzoylamino)butyl)-7-trifluoromethylsulfonyloxy-1,2,3,4-tetrahydroisoquinoline;

2-(4-(4-(3-(5-Methyl-1,2,4-oxadiazolyl)benzoylamino)butyl)-7-trifluoromethylsulfonyloxy-1,2,3,4-tetrahydroisoquinoline;

2-(4-(4-(2-Pyrimidyl)benzoylamino)butyl)-7-trifluoromethylsulfonyloxy-1,2,3,4-tetrahydroisoquinoline;

2-(4-(4-(4-(1-(2-Oxo)pyrrolidinyl)phenyl)benzoylamino)butyl)-7-trifluoromethylsulfonyloxy-1,2,3,4-tetrahydroisoquinoline;

2-(4-(4-(4-Arminosulfonylphenyl)benzoylamino)butyl)-7-trifluoromethylsulfonyloxy-1,2,3,4-tetrahydroisoquinoline;

2-(4-(4-(5-(1-Oxo)indanyl)benzoylamino)butyl)-7-trifluoromethylsulfonyloxy-1,2,3,4-tetrahydroisoquinoline;

2-(4-(3-(6-(1-Pyrrolyl)pyridyl)carboxamido)butyl-7-trifluoromethylsulfonyloxy-1,2,3,4-tetrmhydroisoquinoline;

2-(4-(4-(3-(5-Methyl-1,2,4-oxadiazolyl)-phenylbenzoylamino)butyl)-7-trifluoromethylsulfonyloxy-1,2,3,4-tetrahydroisoquinoline;

2-(4-(4-(2-(5-Methyl-1,3,4-oxadiazolyl)phenylbenzoylamino)butyl)-7-trifluoromethylsulfonyloxy-1,2,3,4-tetrahydroisoquinoline;

2-(4-(4-(3-Methylaznnocarbonyl)phenyl)benzoylamino)butyl-7-trifluoromethylsulfonyloxy-1,2,3,4-tetrahydroisoquinoline;

2-(4-(4-(4-Methylaminocarbonyl)phenyl)benzoylamino)butyl-7-trifluoromethylsulfonyloxy-1,2,3,4-tetrahydroisoquinoline:

2-(4-(4-(4-Pyridyl)benzoylamino)butyl)-7-trifluoromethylsulfonyloxy-1,2,3,4-tetrahydroisoquinoline;

2-(4-(4-(2-Thienyl)benzoylamino)butyl)-7-trifluoromethylsulfonyloxy-1,2,3,4-tetrahydroisoquinoline;

2-(4-(2-(5-(2-Pyridyl)thienylcarboxamido)butyl)-7-trifluoromethylsulfonyloxy-1,2,3,4-tetrahydroisoquinoline;

2-(4-(4-Phenylbenzoylamino)butyl)-7-(3-pyridyl)sulfonyloxy-1,2,3,4-tetrahydroisoquinoline;

2-(4-(4-Phenylbenzoylamino)butyl)-7-(2-cyanophenyl)sulfonyloxy-1,2,3,4-tetrahydroisoquinoline;

2-(4-(4-(Phenylbenzoylamino)butyl)-7-(3-cyanophenyl)sulfonyloxy-1,2,3,4-tetrahydroisoquinoline;

2-(4-(4-Phenylbenzoylamino)butyl)-7-(3-thienyl)sulfonyloxy-1,2,3,4-tetrahydroisoquinoline;

7-Methoxycarbonylmethyl-2-(4-(4-phenylbenzoylamino)butyl)-1,2,3,4-tetrahydroisoquinoline;

7-Ethoxycarbonylmethyl-2-(4-(4-phenylbenzoylarino)butyl)-1,2,3,4-tetrahydroisoquinoline;

7-(2-Cyanophenoxy)-2-(4-(4-phenylbenzoylamino)butyl-1,2,3,4-tetrahydroisoquinoine;

7-Bromo-2-(4-(4-phenylbenzoylamino)butyl)-1,2,3,4-tetrahydroisoquinoline;

7-Cyano-2-(4-(4-phenylbenzoylamino)butyl)-1,2,3,4-tetrahydroisoquinoline;

2-(4-(4-(4-Acetylphenyl)benzoylamino)butyl)-7-trifluoromethoxy-1,2,3,4-tetrahydroisoquinoline;

2-(4-(4-(4-Acetylphenyl)benzoylamino)butyl)-7-trifluoromethyl-1,2,3,4-tetrahydroisoquinoline;

and salts thereof.

The present invention also provides a process for preparing compounds of formula (I) which process comprises:

(a) reacting a compound of formula (II):

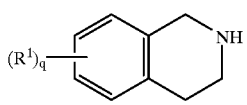

Formula (II)

wherein $R^1$ and q are as hereinbefore defined; with a compound of formula (III):

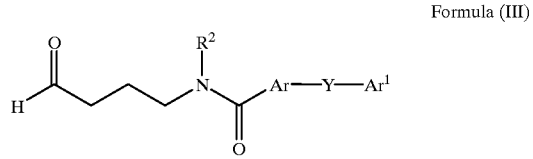

Formula (III)

wherein $R^2$, Y, Ar and $Ar^1$ are as hereinbefore defined;

(b) reaction of a compound of formula (IV):

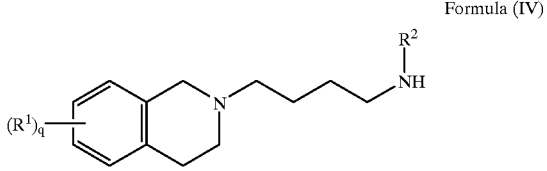

Formula (IV)

wherein $R^1$ and $R^2$ are as hereinbefore defined; with a compound of formula (V):

Formula (V)

wherein Y, Ar and $Ar^1$ art as hereinbefore defined and X is a halogen atom or the residue of an activated ester;

(c) to prepare a compound of formula (I) wherein $R^1$ is $Ar^2$—Z and Z is a bond, reacting a compound of formula (VI):

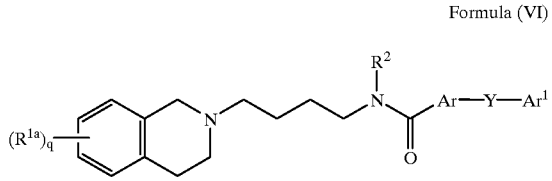

Formula (VI)

wherein one $R^{1a}$ represents a group W wherein W is a halogen atom or a trifluoromethylsulphonyloxy group, or W is a group M selected from a boron derivative e.g. a boronic acid function $B(OH)_2$ or a metal function such as trialkylstannyl e.g. $SnBu_3$, zinc halide or magnesium halide, and when q is 2 the other $R^{1a}$ is $R^1$; with a compound $Ar^2$—$W^1$, wherein $W^1$ is a halogen atom or a trifluoromethylsulphonyloxy group when W is a group M or $W^1$ is a group M when W is a halogen atom or a trifluoromethylsulphonyloxy group;

(d) to prepare a compound of formula (I) wherein $R^1$ is $Ar^2$—Z and Z is O or S, reacting a compound of formula (VII):

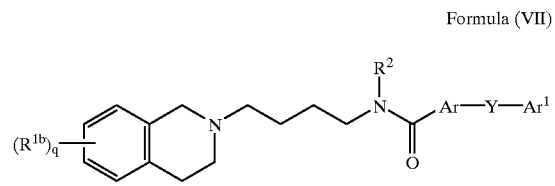

Formula (VII)

wherein one $R^{1b}$ represent a group ZH and when q is 2 the other $R^{1b}$ represents $R^1$; with a reagent serving to introduce the group $Ar^2$;

(e) to prepare a compound of formula (I) where Y is a bond, reaction of a compound of formula (VIII):

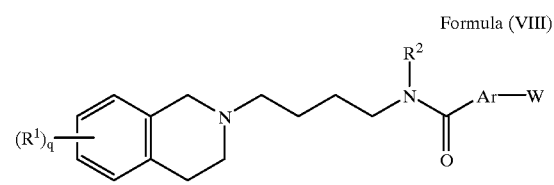

Formula (VIII)

wherein $R^1$, $R^2$, Ar and W are as hereinbefore defined, with a compound $Ar^1$—$W^1$, wherein $W^1$ is a halogen atom or a trifluoromethylsulphonyloxy group when W is a group M, or $W^1$ is a group M when W is a halogen atom or a trifluoromethylsulphonyloxy group.

(f) interconversion of one compound of formula (I) to a different compound of formula (I) e.g. (i) alkylation of a compound (I) wherein $R^2$ represents hydrogen, (ii) conversion of one $R^1$ from alkoxy (e.g.methoxy) to hydroxy, or (iii) conversion of $R^1$ from hydroxy to sulphonyloxy, eg alkylsulphonyloxy or trifluoromethanesulphonyloxy; (iv) conversion of a compound wherein Y represents S to a compound wherein Y is $SO_2$ or (v) conversion of Y from CO to $CH_2$; and optionally thereafter forming a salt of formula (I).

Process (a) requires the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as ethanol.

Process (b) may be effected by methods well known in the art for formation of an amide bond.

Reaction of a compound of formula (VI) with $Ar^2W^1$, according to process (c) or a compound of formula (VIII) with $Ar^1$—$W^1$ according to process (e) may be effected in the presence of a transition metal eg palladium catalyst such as bis-triphenylphosphinepalladium dichloride or tetrakis-triphenylphosphinepalladium (0). When M represents a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulphonyloxy group such as trifluoromethylsulphonyloxy; and $W^1$ is preferably a group M, such as trialkylstannyl or $B(OH)_2$.

In process (d) the reagent serving to introduce the group $Ar^2$ is preferably a compound of formula $Ar^2$—Hal, wherein Hal is a halogen atom. The reaction may be effected in the presence of a base, such as potassium carbonate, in a solvent such as dimethylformamide.

Interconversion reactions according to process (e) may be effected using methods well known in the art.

Compounds of formula (II) may be prepared by methods known in the art.

Compounds of formula (III) are known or may be prepared using standard procedures.

A compound of formula (IV) may be prepared by alkylation of a compound (II) by standard methods. Thus, for example a compound of formula (II) may be reacted with N-(4-bromobutylphthalimide) followed by removal of the phthalimide group to give a compound of formula (TV) where $R^2$ is hydrogen. Compounds where $R^2$ is alkyl may be prepared by subsequent reaction with the appropriate aldehyde using conditions analogous to process (a) above.

Compounds of formula (VI), (VII) or (VIII) may be prepared by processes analogous to (a) or (b) described above. Compounds $Ar^1W^1$, $Ar^2W^1$ and $Ar^2$Hal are commercially available or may be prepared by standard methods.

Compounds of formula (1) have been found to exhibit affinity for dopamine receptors, in particular the $D_3$ receptor, and are expected to be useful in the treatment of disease states which require modulation of such receptors, such as psychotic conditions. Compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant cps. (see for example Sokoloff et al, Nature, 1990; 347: 146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors.

We have found that certain compounds of formula (I) are dopamine $D_3$ receptor antagonists, others may be agonists or partial agonists. The functional activity of compounds of the invention (i.e. whether they are antagonists, agonists or partial agonists) can be readily determined using the test method described hereinafter, which does not require undue experimentation. $D_3$ antagonists are of potential use as antipsychotic agents for example in the treatment of schizophrenia, schizo-affective disorders, psychotic depression and mania. Conditions which may be treated by dopamine $D_3$ receptor agonists include dyskinetic disorders such as Parkinson's disease, neuroleptic-induced parkinsonism and tardive dyskinesias; depression; anxiety, memory disorders, sexual dysfunction and drug (eg. cocaine) dependency.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

A preferred use for $D_3$ antagonists according to the present invention is in the treatment of psychoses such as schizophrenia.

A preferred use for $D_3$ agonists according to the present invention is in the treatment of dyskinetic disorders such as Parkinson's disease.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermnal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil for example polyethylene glycol, polyvinyl pyrrolidone, lecithin, arachis oil or sesame oil. Alternatively, the solution can be lyophilised and then reconstimted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants ($K_i$) of test compounds for displacement of [$^{125}$I] iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @ 37° C.), 20 mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @ 37° C.), using an Ultra-Turrax, and recentrifuged at 18,000 r.p.m for 15 min at 4° C. in a Sorvall RC5C. The membranes were washed two more times with icecold 50 mM Tris salts (pH 7.4 @ 37° C.). The final pellet was resuspended in 50 mM Tris salts (pH 7.4 @ 37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM [$^{125}$I] iodosulpride (~2000 Ci/mmol; Amersham, U.K.), and the test compound in a buffer containing 50 mM Tris salts (pH 7.4 @ 37° C.), 120 mM NaCl, 5 mM KCl, 2 mM CaCl$_2$, 1 mM MgCl$_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @ 37° C.), 120 mM NaCl, 5 mM KCl, 2 mM CaCl$_2$, 1 mM MgCl$_2$. The radioactivity on the filters was measured using a Cobra gamma counter (Canberra Packard). Non-specific binding was defined as the radioligand binding remaining after incubation in the presence of 100 $\mu$M iodosulpride. For competition curves, 14 concentrations (half-log dilutions) of competing cold drug were used. Competition curves were analysed simultaneously whenever possible using non-linear least-squares fitting procedures, capable of fitting one, two or three site models.

Compounds of Examples tested according to this method had pKi values in the range 7.0 to 9.0 at the human dopamine $D_3$ receptor.

Functional Activity at Cloned Dopamine Receptors

The functional activity of compounds at human D2 and human D3 receptors (ie agonism or antagonism) may be determined using a Cytosensor Microphysiometer (McConnell HM et al Science 1992 257 1906–1912) In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5% CO$_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90s. The pump was on for the first 60s and the acidification rate determined between 68 and 88s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each putative agonist concentration was determined and concentration-response curves fitted using Robofit [Tilford, N. S., Bowen, W. P. $\mu$Baxter, G. S. Br. J. Pharmacol. (1995) in press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Compounds of Examples 8(*b*) and 8(*t*) tested as antagonists according to this method had pKb values in the range 8.3–9 at the human dopamine $D_3$ receptor.

Pharmaceutical Formulations

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.
Solvent: Typically water but may also include cyclodextfins (1–100 mg) and co-solvents such as propylene glycol, polyethylene glycol and alcohol.

| Tablet | |
|---|---|
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins

Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl funarate.
Oral Suspension

| Oral Suspension | |
|---|---|
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose
Diluent: e.g. sorbitol solution, typically water
Preservative: e.g. sodium benzoate
Buffer: e.g. citrate
Co-solvent: e.g. alcohol, propylene glycol, polyethylene glycol, cyclodextrin The invention is further illustrated by the following non-limiting examples:

DESCRIPTION 1

N-(4-Hydroxybutyl)-4-phenylbenzamide

To a stirred solution of 4-amino-1-butanol (7.34 g, 82 mmol) and triethylamine (12.3 ml; 8.82 g, 87 mmol) in dichloromethane (100 ml) at 0° C. was added a solution of 4-phenylbenzoyl chloride (18.36 g, 85 mmol) in dichloromethane (800 ml) dropwise over 1.2 h. Resultant was stirred at 0° C. for 2 h then at room temperature for 18 h. The resulting white solid was filtered off (15.94 g) and the filtrate washed with 5% aqueous sodium hydroxide (1L). The organic phase was dried ($Na_2SO_4$) and evaporated in vacuo to give a white solid (4.96 g) which was combined with the above to give the title compound (20.9 g, 93%).

$^1$H NMR (DMSO-$d_6$) δ: 1.4–1.7 (4H, m), 3.26 (2H, q, J=7 Hz), 3.42 (2H, q, J=7 Hz), 4.43 (1H, t, J=6 Hz), 7.35–7.55 (3H, m), 7.75 (4H, m), 7.94 (2H, d, J=9 Hz), 8.52)1H, t, J=7 Hz)

DESCRIPTION 2

4-(4-Phenylbenzoylamino)butyraldehyde

To a mechanically-stirred solution of N-(4-hydroxybutyl)-4-phenylbenzamide (11.2 g, 44.2 mmol) and triethylamine (148 ml; 107.5 g, 1.06 mol) in dimethyl sulfoxide (250 ml) at room temperature was added, dropwise over 1 h, a solution of pyridine-sulfur trioxide complex (43.7 g, 0.273 mol) in dimethyl sulfoxide (200 ml) with external cooling using a cold water bath. The mixture was stirred at room temperature for 3 h, then 2M hydrochloric acid (550 ml) was added slowly with ice cooling. Resultant was diluted with water (1L) then extracted with ethyl acetate (3×500 ml). The combined extracts were washed with 2M hydrochloric acid (3×500 ml) and water (3×500 ml) then dried ($Na_2SO_4$) and evaporated in vacuo to give a semi solid (12 g). Chromatography on silica gel eluting with 10–100% ethyl acetate-hexane gave the title compound as a white solid (4.72 g, 42%).

$^1$H NMR (CDCl$_3$) δ: 2.00 (2H, m), 2.65 (2H, m), 3.52 (2H, q, J=8 Hz), 6.54 (1H, br m), 7.35–7.53 (3H, m), 7.54–7.71 (4H, m), 7.85 (2H, m), 9.83 (1H, s)

DESCRIPTION 3

4-Phthalimidobutyraldehyde Diethyl Acetal

A solution of 4-aminobutyraldehyde diethyl acetal (48.5 g, 0.3 mol) in tetrahydrofuran (60 ml) was added dropwise to a stirred slurry of N-(ethoxycarbonyl) phthalimide (65.93 g, 0.3 mol) in tetrahydrofuran (250 ml) at 0° C. After stirring at 0° C. for 0.16 h and at room temperature for 18 h the solvent was removed in vacuo and the residue distilled at 1 mmHg to remove the ethyl carbamate by-product. The residual brown oil was allowed to cool to afford the title compound (91 g, 93%).

Mass spectrum (API$^+$): 218 (MH$^+$ for aldehyde).

$^1$H NMR (CDCl$_3$) δ: 1.20 (6H, t, J=7 Hz), 1.70 (4H, m), 3.35–3.85 (6H, m), 4.55 (1H, t, J=5 Hz), 7.70 (2H, m), 7.85 (2H, m).

DESCRIPTION 4

4-Phthalimidobutyraldehyde

A solution of 4-phthalimidobutyraldehyde diethyl acetal (125 g, 0.43 mol) in a 1:1 mixture of tetrahydrofuran and 2N hydrochloric acid (800 ml) was heated at reflux for 0.75 h. The mixture was cooled, concentrated to 400 ml and extracted into dichloromethane (3×200 ml). Combined organics were dried ($Na_2SO_4$) and evaporated in vacuo to afford the title compound as a brown oil that solidified on standing (95 g, 100%).

Mass spectrum API$^+$): 218 (MH$^+$), $C_{12}H_{11}NO_3$ requires 217.

$^1$H NMR (CDCl$_3$) δ: 2.00 (2H, m), 2.55 (2H, t, J=5 Hz), 3.75 (2H, t, J=5 Hz), 7.70 (2H, m), 7.85 (2H, m), 9.30 (1H, s).

DESCRIPTION 5

7-Methoxy-2-(4-phthalimidobutyl)-1,2,3,4-tetrahydroisoquinoline

Prepared from 4-phthalimidobutyraldehyde (15.96 g, 0.074 mol) and 7-methoxy-1,2,3,4-tetrahydroisoquinoline (10 g, 0.061 mol) using a procedure similar to that of Example 1 (13.5 g, 60%).

Mass spectrum (API$^+$): 365 (MH$^+$) C$_{22}$H$_{24}$N$_2$O$_3$ requires 364.

$^1$H NMR (CDCl$_3$) δ: 1.70 (4H, m), 2.50 (2H, m), 2.70 (2H, m), 2.80 (2H, m), 3.55 (2H, s), 3.55–3.80 (5H, m), 6.55 (1H, d, J=2 Hz), 6.70 (1H, dd, J=2 Hz, 8 Hz), 7.00 (1H, d, J=8 Hz), 7.70 (2H, m), 7.85 (2H, m).

DESCRIPTION 6

2-(4-Aminobutyl)-7-methoxy-1,2,3,4-tetrahydroisoquinoline

A solution of 7-methoxy-2-(4-phthalimidobutyl)-1,2,3,4-tetrahydroisoquinoline (17.4 g 0.0478 mol) and hydrazine monohydrate (4.6 ml, 0.095 mol) in ethanol (300 ml) were stirred at room temperature for 18 h and at reflux for 1 h. The cooled reaction mixture was filtered and the filtrate evaporated in vacuo. The residue was dissolved in 2.5N hydrochloric acid, filtered through Kieselguhr and the filtrate basified with 0.880 ammonia. The product was extracted into dichloromethane (4×200 ml), the combined extracts were dried (Na$_2$SO$_4$) and evaporated in vacuo to afford the title compound as a brown oil (7 g, 63%).

Mass spectrum (API$^+$): 235 (MH$^+$) C$_{14}$H$_{22}$N$_2$O requires 234.

$^1$H NMR (CDCl$_3$) δ: 1.30–1.90 (4H, m), 2.50 (2H, m), 2.60–2.90 (8H, m), 3.60 (2H, s), 3.75 (3H, s), 6.55 (1H, d, J=2 Hz), 6.70 (1H, dd, J=2 Hz, 8 Hz), 7.00 (1H, d, J=8 Hz).

DESCRIPTION 7

7-Hydroxy-2-(4-phthalimidobutyl)-1,2,3,4-tetrahydroisoquinoline

Prepared from 7-methoxy-2-(4-phthalimidobutyl)-1,2,3,4-tetrahydroisoquinoline (1.45 g, 3.98 mmol) using a procedure similar to that of Example 2 (1.31 g, 94%).

Mass spectrum (API$^+$): 351 (MH$^+$) C$_{21}$H$_{22}$N$_2$O$_3$ requires 350.

$^1$H NMR (CDCl$_3$) δ: 1.70 (4H, m), 2.25–2.85 (1H, br s), 2.50 (2H, t, J=7 Hz), 2.70 (2H, d, J=4 Hz), 2.85 (2H, d, J=4 Hz). 3.50 (2H, s), 3.75 (2H, t, J=7 Hz), 6.45 (1H, d, J=2 Hz), 6.60 (1H, dd, J=2 Hz, 8 Hz), 6.90 (1H, d, J=8 Hz), 7.70 (2H, m), 7.85 (2H, m).

DESCRIPTION 8

2-(4-Phthalimidobutyl)-7-trifluoromethylsulfonyloxy-1,2,3,4-tetrahydroisoquinoline Trifluoromethanesulfonic anhydride (0.53 ml, 3.14 mmol) was added dropwise with stirring to an ice-cooled solution of 7-hydroxy-2-(4-phthalimidobutyl)-1,2,3,4-tetrahydroisoquinoline (1 g, 2.86 mmol) in anhydrous pyridine (10 ml). After stirring at room temperature for 18 h the reaction mixture was added to 10% aqueous Copper (II) sulfate (100 ml) and extracted into ethyl acetate (200 ml). The organic layer was separated, washed with 10% aqueous copper (II) sulfate (2×50 ml), dried (Na$_2$SO$_4$) and evaporated in vacuo. Chromatography on silica gel using 10–100% ethyl acetate-hexane gradient elution gave the title compound as a green oil (0.45 g, 33%).

Mass spectrum (API$^+$): 483 (MH$^+$). C$_{22}$H$_{21}$F$_3$N$_2$O$_5$S requires 482.

$^1$H NMR (CDCl$_3$) δ: 1.75 (4H, m), 2.55 (2H, t, J=7 Hz), 2.75 (2H, t, J=6 Hz), 2.90 (2H, t, J=6 Hz), 3.60 (2H, s), 3.75 (2H, t, J=7 Hz), 6.90 (1H, d, J=2 Hz), 7.05 (1H, dd, J=2 Hz, 9 Hz), 7.15 (1H, d, J=9 Hz), 7.70 (2H, m), 7.85 (2H, m).

DESCRIPTION 9

2-(4-Aminobutyl)-7-trifluoromethylsulfonyloxy-1,2,3,4-tetrahydroisoquinoline Prepared from 2-(4-phthalimidobutyl)-7-trifluoromethylsulfonyloxy-1,2,3,4-tetrahydroisoquinoline (0.44 g, 0.91 mmol) using a procedure similar to that of Description 6 (0.26 g, 81%).

Mass spectrum (API$^+$): 353 (MH$^+$). C$_{14}$H$_{19}$F$_3$N$_2$O$_3$S requires 352.

$^1$H NMR (CDCl$_3$) δ: 1.50 (6H, m), 2.50 (2H, t, J=7 Hz), 2.75 (4H, m), 2.90 (2H, t, J=6 Hz), 3.60 (2H, s), 6.90 (1H, d, J=2 Hz), 7.0 (1H, dd, J=2 Hz, 9 Hz), 7.15 (1H, d, J=9 Hz).

DESCRIPTION 10

4-Bromobenzamidoxime

To a stirred solution of ice cooled methanol (115 ml), under argon, was added potassium tert-butoxide (10.12 g. 0.09 mol), portionwise. After stirring for 5 minutes hydroxylamine hydrochloride (6.71 g, 0.097 mol) was added in one portion. After stirring for 1 hour at room temperature a slurry of 4-bromobenzonitrile, (10.88 g, 0.06 mol) in methanol (150 ml) was added. The mixture was then heated at reflux for 4 hours, cooled and filtered. The filtrate was evaporated in vacuo to give the title compound as a colourless solid (14.12 g, quant.)

Mass spectrum (API$^+$): Found 215 and 217 (MH$^+$). C$_7$H$_7$BrN$_2$O requires 214 and 216.

DESCRIPTION 11

3-(4-Bromophenyl)-5-methyl-1,2,4-oxadiazole

4-Bromobenzamidoxime (13.05 g, 0.061 mol) was heated at reflux in acetic anhydride (60 ml) for 3 hours. The mixture was cooled and poured into ice-water (200 ml) and extracted into dichloromethane (2×200 ml). The organic layer was washed with water (100 ml), dried (Na$_2$SO$_4$), and evaporated. The residue was partitioned between ether (200 ml) and water (200 ml). The ether layer was dried (Na$_2$SO$_4$) and evaporated in vacuo to give a yellow solid (13.89 g) which was chromatographed on silica gel eluting with 10–20% ethyl acetate/hexane to give the title compound as a colourless solid (8.94 g, 0.037 mol, 61%).

Mass spectrum (API$^+$): Found 239 and 241 (MH$^+$). C$_9$H$_7$BrN$_2$O requires 238 and 240.

DESCRIPTION 12

4-(4-(3-(5-Methyl-1,2,4-oxadazolyl))phenyl)Benzoic Acid

A mixture of 3-(4-bromophenyl)-5-methyl-1,2,4-oxadiazole (4.35 g, 0.018 mol), 4-carboxybenzeneboronic acid (3 g, 0.018 mol), palladium tetralistriphenylphosphine (0) (270 mg, 0.23 mmol), sodium carbonate (6.8 g, 0.064 mol) in a 1:1 mix of 1,2-dimethoxyethane and water (260 ml), was heated at reflux, under argon, for 16 hours. The mixture was cooled and treated with ether (150 ml), and the aqueous phase separated and acidified to pH5 with 5N HCl. The precipitated solid was filtered and dried to give the title compound as a beige solid (1.17 g, 4.18 mmol, 23%).

Mass spectrum (API$^+$): Found 279 (M−H)$^−$. $C_{16}H_{12}N_2O_3$ requires 280.

The following compounds were prepared in a manner similar to Description 12

(a) 4-(4-(1-(2-Oxo)pyrrolidinyl)phenyl)benzoic acid
Mass spectrum (API$^+$): Found 280 (M−H)$^−$. $C_{17}H_{15}NO_3$ requires 281.

(b) 4-(3-Acetylphenyl)benzoic acid
$^1$H NMR (DMSO) δ: 2.70 (3H, s), 3.00–4.50 (1H, br s), 7.70 (1H, t, J=8 Hz), 7.90 (2H, d, J=8 Hz), 8.05 (2H, dd, J=8 Hz, 2 Hz), 8.10 (2H, d, J=8 Hz), 8.25 (1H, s).

(c) 4-(4-(1-Methyl)pyrazolyl)benzoic add
Mass spectrum API$^+$): Found 203 (MH$^+$). $C_{11}H_{10}N_2O_2$ requires 202.

(d) 4-(5-(1-Oxo)indanyl)benzoic acid
Mass spectrum API$^+$): Found 251 (M−H)$^−$. $C_{16}H_{12}O_3$ requires 252.

(e) 4-(3-(6-Methyl)pyridyl)benzoic acid
Mass spectrum (API$^+$): Found 214 (MH$^+$). $C_{13}H_{11}NO_2$ requires 213.

(f) 4-(2-Pyrimidyl)benzoic acid
$^1$H NMR (DMSO) δ: 7.52 (1H, t, J=5 Hz), 8.08 (2H, d, J=11 Hz), 8.50 (2H, d, J=11 Hz), 8.97 (2H, d, J=5 Hz).

(g) 4-(4-Aminosulfonyl)phenylbenzoic acid
$^1$H NMR (DMSO) δ: 7.48 (2H, s), 7.88 (2H, d, J=10 Hz), 7.95 (4H, s), 8.08 (2H, d, J=10 Hz), 13.15 (1H, br s).

(h) 4-(3-Methylsulfonyl)phenylbenzoic acid
$^1$H NMR (CDCl$_3$) δ: 3.30 (3H, s), 7.80 (1H, t, J=7 Hz), 7.95 (3H, m), 8.10 (3H, m), 8.25 (1H, s), 13.10 (1H, br s).

(i) 4-(4-(2-(5-Methyl-1,3,4-oxadiazolyl))phenyl)benzoic acid
Mass spectrum (API$^+$): Found 279 (M−H)$^−$. $C_{16}H_{12}N_2O_3$ requires 280.
$^1$H NMR (DMSO) δ: 2.62 (3H, s), 7.93 (3H, m), 8.06 (5H, m)

(j) 4-(3-Aminocarbonyl)phenylbenzoic acid
Mass spectrum (API$^+$): Found 240 (M−H)$^−$. $C_{14}H_{11}NO_3$ requires 241.

(k) 4-(3-Thienyl)benzoic acid
$^1$H NMR (DMSO) δ: 7.60–7.70 (2H, m), 7.85 (2H, d, J=10 Hz), 7.98 (2H, d, J=10 Hz), 8.03–8.10 (1H, m), 13.00 (1H, br s).

(l) 4-(4Pyridyl)benzoic acid
Mass spectrum (API$^+$): Found 198 (M−H)$^−$. $C_{12}H_9NO_2$ requires 199.

DESCRIPTION 13

1-(4-Bromophenyl)-2-pyrrolidinone

To a solution of 4-bromoaniline (10 g, 58 mmol) in dry THF (150 ml), under argon was added triethylamine (6 g, 59 mmol) and 4-chlorobutyryl chloride (8.2 g 58 mmol) at 5° C. The mixture was stirred at 5° C. for 40 mins and potassium tert-butoxide (16 g, 142 mmol) added in one portion. After 10 mins the mixture was warmed to 25° C. and stirred for 4 hours, then left to stand overnight. Water (10 ml) was added and the mixture stirred for 30 mins. The mixture was diluted with ethyl acetate (200 ml) and 3% Na2CO$_3$ (aq) (120 ml). The aqueous layer was reextracted with ethyl acetate (100 ml) and the combined extracts dried over Na$_2$SO$_4$. The solvent was evaporated in vacuo to give a brown solid (12 g). Chromatography on silica gel (~200 g) using 30–60% ethyl acetate/hexane gradient elution gave the tide compound as a yellow crystalline solid (10.24 g, 74%).

Mass spectrum (API$^+$): Found 240 and 242 (MH$^+$). $C_{10}H_{10}BrNO$ requires 239 and 241.

DESCRIPTION 14

2-(4-Bromophenyl)-5-methyl-1,3,4-oxadiazole

A stirred suspension of 4-bromobenzoic hydrazide (4.0 g, 18.6 mmol) in triethyl orthoacetate (15 ml) was heated under reflux for 24 h. The reaction mixture was cooled and the precipitate filtered, washed with 60–80° C. petroleum ether (20 ml) and dried to give the title compound as a yellow solid (3.86 g, 87%).

Mass spectrum (API$^+$): Found 239 and 241 (MH$^+$). $C_9H_7BrN_2O$ requires 238 and 240.
$^1$H NMR (CDCl$_3$) δ: 2.62 (3H, s), 7.64 (2H, m), 7.90 (2H, m).

DESCRIPTION 15

(4-Trifluoroacetamido)Butyraldehyde

To a solution of 4-aminobutyraldehyde diethyl acetal (16.10 g, 0.10 mmol) and triethylamine (18.06 ml, 0.12 mol) in dichloromethane (150 ml) at 0° C. was added a solution of trifluoroacetic anhydride (16.9 ml, 0.11 mol) in dichloromethane (60 ml). The reaction mixture was warmed to room temperature and stirred for 3 h, then partitioned between 5% aq NaHCO$_3$ (400 ml) and dichloromethane (400 ml). The aqueous layer was extracted further with dichloromethane (3×100 ml), the combined extracts were dried (Na$_2$SO$_4$) and evaporated in vacuo to afford a pale yellow oil which was added to a stirred mixture of TBF (300 ml) and water (500 ml). 5N Sulfuric acid (2.27 ml) was added and the reaction mixture left to stir at room temperature for 18 h. Saturated aqueous sodium bicarbonate (500 ml) was added and the product was extracted into dichloromethane (4×100 ml). The combined organic extracts were dried (Na$_2$SO$_4$) and evaporated in vacuo to afford the title compound as a yellow oil (15.42 g, 65%).

$^1$H NMR (CDCl$_3$) δ: 1.95 (2H, m), 2.62 (2H, t, J=8 Hz), 3.38 (2H, m), 7.54–7.80 (1H, br s), 9.77 (1H, s).

DESCRIPTION 16

(4-Trifluoromethoxy)Phenylethylamine Hydrochloride

To a stirred solution of zirconium (IV) chloride (58.8 g, 250 mmol) in dry tetrahydrofuran (750 ml) at 20° C. under argon was added, portionwise, sodium borohydride (37.6, 1.0 mol). Mixture was stirred for 1 h, then 4-trifluoromethoxyphenylacetonitrile (20.0 g, 100 mmol) was added. Stirring was continued for 24 h, then water (310 ml) was added dropwise, keeping the internal temperature below 10° C. The mixture was partitioned between dilute aqueous ammonia (200 ml) and ethyl acetate (3×300 ml). Organic extracts were dried (Na$_2$SO$_4$) and evaporated in vacuo to give an oil which was treated with ethereal HCl to give the title compound (13.53 g. 57%).

Mass spectrum (API$^+$): Found 206 (MH$^+$). C$_9$H$_{10}$F$_3$NO requires 205.

The following compound was prepared in a similar manner go description 16.

(a) (4-Trifluoromethyl)phenethylamine hydrochloride

Mass spectrum (API$^+$): Found 190 (MH$^+$). C$_9$H$_{10}$F$_3$N requires 189.

DESCRIPTION 17

N-(2-(4-Trifluoromethoxyphenyl)ethyl) Trifluoroacetamide

To a stirred mixture of (4-trifluoromethoxy)phenethylamine hydrochloride (13.53 g, 56 mmol) and 2,6-lutidine (13.1 ml; 12.05 g, 113 mmol) in dichloromethane (200 ml) at 0° C. under argon was added, dropwise, trifluoroacetic anhydride (8.1 ml, 12.04 g, 57.4 mmol). Resultant was stirred at 20° C. for 18 h then partitioned between water (200 ml) and dichloromethane (2×200 ml). Organic phase was washed with 1M hydrochloric acid (150 ml), saturated aqueous NaHCO$_3$ (100 ml), dried (Na$_2$SO$_4$) then evaporated in vacuo to give the title compound (13.94 g, 81%) as a solid.

Mass spectrum (API$^-$): Found 300 (M–H)$^-$. C$_{11}$H$_9$F$_6$NO$_2$ requires 301.

The following compound was prepared in a similar manner to description 17.

(a) N-(2-(4-Trifluoromethylphenyl)ethyl) trifluoroacetamide

Mass spectrum (API$^-$): Found 284 (M–H)$^-$. C$_{11}$H$_9$F$_6$NO requires 285.

DESCRIPTION 18

7-Trifluoromethoxy-1,2,3,4-tetrahydroisoquinoline

N-(2-(4-Trifluoromethoxyphenyl)ethyl) trifluoroacetamide (13.94 g, 46.3 mmol) was treated in a manner similar to that described in G. E. Stokker, Tetrahedron Letters 37 5453 1996. The resulting product (13.8 g) was treated with anhydrous potassium carbonate (32.0 g, 0.232 mol) in methanol (400 ml) containing water (40 ml) at reflux for 2 h. The mixture was cooled, evaporated in vacuo, then partitioned between water (400 ml) and dichloromethane (2×200 ml). Combined organic extracts were dried (Na$_2$SO$_4$) and evaporated in vacuo to give the tide compound (9.05 g, 95%) as an oil.

Mass spectrum (API$^+$): Found 218 (MH$^+$). C$_{10}$H$_{10}$F$_3$NO requires 217.

The following compound was prepared in a similar manner to description 18.

(a) 7-Trifluoromethyl-1,2,3,4-tetrahydroisoquinoline

Mass spectrum (API$^+$): Found 202 (MH$^+$). C$_{10}$H$_{10}$F$_3$N requires 201.

DESCRIPTION 19

2-(4-Trifluoroacetamido)butyl-7-trifluoromethoxy-1,2,3,4-tetrahydroisoquinoline

A mixture of 7-trifluoromethoxy-1,2,3,4-tetrahydroisoquinoline (8.54 g, 39.4 mmol), (4-Trifluoroacetamido)butyraldehyde (7.20 g, 39.4 mmol), and sodium triacetoxyborohydride (12.53 g, 59.1 mmol) in dichloroethane (400 ml) was stirred at 20° C. for 18 h. Resultant was partitioned between saturated aqueous NaHCO$_3$ (700 ml) and dichloromethane (2×200 ml). Combined organic extracts were dried (Na$_2$SO$_4$) and evaporated in vacuo to give an oil (13.4 g). Chromatography on silica eluting with 10–70% ethyl acetate-hexane gave the title compound (8.69 g, 57%) as an oil.

Mass spectrum (API$^-$): Found 383 (M–H)$^-$. C$_{16}$H$_{18}$F$_6$N$_2$O$_2$ requires 384.

The following compound was prepared in a similar manner to description 19

(a) 2-(4-Trifluoroacetamido)butyl-7-trifluoromethyl-1,2,3,4-tetrahydroisoquinoline Mass spectrum (API$^+$): Found 369 (MH$^+$). C$_{16}$H$_{18}$F$_6$N$_2$O requires 368.

DESCRIPTION 20

2-(4-Aminobutyl)-7-trifluoromethoxy-1,2,3,4-tetrahydroisoquinoline

A mixture of 2-(4-Trifluoroacetamido)butyl-7-trifluoromethoxy-1,2,3,4-tetrahydroisoquinoline (8.68 g, 22.6 mmol), anhydrous potassium carbonate (16.0 g, 116 mmol), water (25 ml) and methanol (250 ml) was heated at reflux for 1 h, cooled, then evaporated in vacuo. Residue was partitioned between water (100 ml) and dichloromethane (3×100 ml) and the combined extracts were dried (Na$_2$SO$_4$) then evaporated in vacuo to give the title compound (5.75 g, 88%) as an oil.

Mass spectrum (API$^+$): Found 289 (MH$^+$). C$_{14}$H$_{19}$F$_3$N$_2$O requires 288.

The following compound was prepared using a method similar to description 20.

(a) 2-(4-Aminobutyl)-7-trifluoromethyl-1,2,3,4-tetrahydroisoquinoline

Mass spectrum (API$^+$): Found 273 (MH$^+$). C$_{14}$H$_{19}$F$_3$N$_2$ requires 272.

EXAMPLE 1

7-Methoxy-N-(4-(4-phenylbenzoylamino)butyl)-1,2,3,4-tetrahydroisoquinoline.

Sodium triacetoxyborohydride (4.66 g, 22 mmol) was added to a stirred mixture of 4-(4-phenylbenzoylamino)butyraldehyde (3.92 g, 15 mmol) and 7-methoxy-1,2,3,4-tetrahydroisoquinoline [Daniel J. Sall et al., J. Med. Chem., 1987, 30, 2208] (2.40 g, 14.7 mmol) in 1,2-dichloroethane (200 ml) at room temperature. After stirring for 16 h, dichloromethane (100 ml) was added and the mixture was then washed with saturated aqueous K$_2$CO$_3$ (2×100 ml) and brine (100 ml). Drying (Na$_2$SO$_4$) and evaporation in vacuo afforded a viscous oil which was chromatographed on silica gel, eluting with ethyl acetate, to give the title compound as a pale pink solid (5.04 g, 83%).

Mass spectrum (API$^+$): 415 (MH$^+$)

$^1$H NMR (CDCl$_3$) δ: 1.77 (4H, m), 2.56 (2H, m), 2.72 (2H, m), 2.81 (2H, m), 3.54 (4H, m), 3.68 (3H, s), 6.51 (1H, d, J=3 Hz), 6.72 (1H, dd, J=3 and 8 Hz), 7.02 (1H, d, J=8 Hz), 7.26–7.74 (9H, bm), 7.76 (1H, bt, J=5 Hz).

EXAMPLE 2

7-Hydroxy-N-(4-(4-phenylbenzoylamino)butyl)-1,2,3,4-tetrahydroisoquinoline.

A solution of borontribromide in dichloromethane (72 ml, 1M solution, 72 mmol) was added dropwise with stirring to an ice-cooled solution of 7-methoxy-N-(4-(4-phenylbenzoylamino)butyl)-1,2,3,4-tetrahydroisoquinoline (5.00 g, 12.1 mmol) in dichloromethane (150 ml). After stirring at room temperature for 16 h the reaction mixture was poured onto a mixture of crushed-ice (200 g) and 0.880 aqueous ammonia (400 ml). The resulting mixture was extracted with dichloromethane (3×200 ml). The combined organics were washed with brine (200 ml) then dried ($Na_2SO_4$) and the solvent evaporated in vacuo to give the title compound as a pale yellow solid (3.60 g, 75%).

Mass spectrum API$^+$): 401 (MH$^+$)

$^1$H NMR (CDCl$_3$) δ: 1.52 (4H, m), 2.40–2.90 (6H, bm). 3.45 (4H , m), 6.47 (1H, d, J=3 Hz), 6.64 (1H, dd, J=3 and 8 Hz), 6.86 (1H, d, J=8 Hz), 7.28–7.85 (10H, bm).

The following compounds were prepared in a similar manner to Example 2

(a) 2-(4-(4-(4-Cyanophenyl)benzoylamino)butyl)-7-hydroxy-1,2,3,4-tetrahydroisoquinoline Mass spectrum (API$^+$): 426 (MH$^+$). $C_{27}H_{27}N_3O_2$ requires 425.

$^1$H NMR (CDCl$_3$) δ: 1.75 (4H, br m), 2.55 (2H, br m), 2.75 (4H, m), 3.45 (2H, s), 3.55 (2H m),6.35(1H, d, J=2 Hz), 6.65(1H, dd, J=2 Hz, 8 Hz), 6.90 (1H d, J=8 Hz), 7.35 (2H, d, J=8 Hz), 7.70 (7H, m), 7.85 (1H, t, J=5 Hz).

(b) 2-(4-(4-(4-Acetylphenyl)benzoylamino)butyl)-7-hydroxy-1,2,3,4-tetrahydroisoquinoline Mass spectrum API$^+$): 443 (MH$^+$) $C_{28}H_{30}N_2O_3$ requires 442.

$^1$H NMR (CDCl$_3$) δ: 1.70 (4H, br m), 2.50 (2H, br m), 2.55 (3H, s), 2.75 (4H, br m), 3.40 (2H, s), 3.50 (2H, m), 6.35 (1H, d, J=2 Hz), 6.65 (1H, dd, J=2 Hz, 8 Hz), 6.85 (1H, d, J=8 Hz), 7.40 (2H, d, J=8 Hz), 7.70 (6H, m), 8.00 (2H, d, J=8 Hz).

EXAMPLE 3

N-(4-(4-Phenylbenzoylamino)butyl)-7-trifluoromethylsulfonyloxy 1,2,3,4-tetrahydroisoquinoline, Hydrochloride.

Trifluoromethanesulfonic anhydride (0.24 ml, 1.4 mmol) was added dropwise with stirring to an ice-cooled solution of 7-hydroxy-N-(4-(4-phenylbenzoylamino)butyl)-1,2,3,4-tetrahydroisoquinoline (0.50 g, 1.3 mmol) in dry pyridine (8.0 ml). After stirring at room temperature for 16 h the reaction mixture was diluted with ethyl acetate (100 ml) and was then washed with a saturated aqueous solution of Copper (II) sulfate (6×50 ml) and brine (50 ml). Drying (Na$_2$SO4) and evaporation of the solvent in vacuo afforded an orange oil which was chromatographed on silica gel, eluting with ethyl acetate, to give a yellow solid (0.19 g, 27%). Treatment with HCl-ether gave the title compound as a yellow powder.

Mass spectrum (API$^+$): 533 (MH$^+$)

$^1$H NMR (CDCl$_3$) δ: 1.75 (4H, bm), 2.57 (2H, m), 2.75 (2H, m), 2.88 (2H, m), 3.52 (2H, m), 3.64 (2H, s), 6.95–7.15 (4H, m), 7.30–7.80 (9H, m). (Free base).

EXAMPLE 4

7-Methylsulfonyloxy-N-(4-(4-phenylbenzoylamino) butyl)-1,2,3,4-tetrahydroisoquinoline, Hydrochloride.

Methanesulfonyl chloride (0.26 ml, 3.3 mmol) was added dropwise with staining to an ice-cooled solution of 7-hydroxy-N-(4-(4phenylbenzoylamino)butyl)-1,2,3,4-tetrahydroisoquinoline (0.50 g, 1.3 mmol) and triethylamine (0.23 ml, 1.6 mmol) in dichloromethane (20 ml). After stirring at room temperature for 16 h the reaction mixture was washed with saturated aqueous K$_2$CO$_3$ (2×10 ml) and brine (10 ml). Drying (Na2SO$_4$) and evaporation of the solvent in vacuo afforded a yellow solid which was chromatographed on silica, eluting with 10% methanol in ethyl acetate, to give a pale yellow solid (0.24 g, 39%). Treatment with HCl-ether gave the title compound as a pale yellow powder.

Mass Spectrum (API$^+$): 479 (MH$^+$)

$^1$H NMR (CDCl$_3$) δ: 1.75 (4H, m), 2.58 (2H, m), 2.75 (2H, m), 2.88 (2H, m), 3.05 (3H, s), 3.52 (2H, m), 3.62 (2H, s), 6.95 (1H, d, J=2 Hz), 7.08 (3H, m), 7.30–7.54 (7H, bm), 7.75 (2H, d, J=10Hz) (Free base).

EXAMPLE 5

2-(4-(4-(3Cyanophenyl)benzoylamino)butyl)-7-methoxy-1,2,3,4-tetrahydroisoquinoline 1-Ethyl-3-(3-dimethylaminopropyl)carbodiimide hydrochloride (0.41 g, 2.14 mmol) was added to a solution of 2-(4-aminobutyl)-7-methoxy-1,2,3,4-tetrahydroisoquinoline (0.5 g, 2.14 mmol), 4-(3-cyanophenyl)benzoic acid (0.368 g, 2.14 mmol) and 1-hydroxybenzotriazole (0.1 g, 0.7 mmol) in dichloromethane (8 ml). The resultant mixture was shaken for 18 h. before saturated aqueous potassium carbonate (5 ml) was added and shaking continued 1 hr. The organic layer was chromatographed on silica gel using 10–100% ethyl acetate-hexane gradient elution to afford the title compound as a yellow gum (0.57 g, 61%).

Mass spectrum (API$^+$): 440 (MH$^+$) $C_{28}H_{29}N_3O_2$ requires 439.

$^1$H NMR (CDCl$_3$) δ: 1.75 (4H, m), 2.60 (2H, br m), 2.75 (2H, t, J=7 Hz), 2.85 (2H, t, J=7 Hz), 3.50 (2H, m), 3.60 (2H, s), 3.75 (3H, s), 6.50 (1H, d, J=2 Hz), 6.60 (1H, dd, J=2 Hz, 8 Hz), 7.00 (1H, d, J=8 Hz), 7.25 (2H, d, J=9 Hz), 7.55 (1H, t, J=7 Hz), 7.65 (3H, m), 7.75 (2H, m), 8.10 (1H, br m).

The following compounds were prepared in a similar manner to Example 5.

(a) 2-(4-(4-(4-Cyanophenyl)benzoylamino)butyl)-7-methoxy-1,2,3,4-tetrahydroisoquinoline Mass spectrum (API$^+$): 440 (MH$^+$). $C_{28}H_{29}N_3O_2$ requires 439.

$^1$H NMR (CDCl$_3$) δ: 1.80 (4H, m), 2.60 (2H, m), 2.75 (2H, t, J=7 Hz), 2.85 (2H, t, J=7 Hz), 3.50 (2H, m), 3.55 (2H, s), 3.70 (3H, s), 6.5 (1H, d, J=2 Hz), 6.70 (1H, dd, J=2 Hz, 8 Hz), 7.05 (1H, d, J=8 Hz), 7.30 (2H, d, J=8 Hz), 7.65 (6H, m), 8.05 (1H, br m).

(b) 2-(4-(4-(4-Acetylphenyl)benzoylamino)butyl)-7-methoxy-1,2,3,4-tetrahydroisoquinoline Mass spectrum (API$^+$): 457 (MH$^+$). $C_{29}H_{32}N_2O_3$ requires 456.

$^1$H NMR (CDCl$_3$) δ: 1.80 (4H, m), 2.60 (2H, m), 2.65 (3H, s), 2.75 (2H, t, J=7 Hz), 2.85 (2H, t, J=7 Hz), 3.50 (2H, m), 3.60 (2H, s), 3.70 (3H, s), 6.50 (1H, d, J=2 Hz), 6.70 (1H, dd, J=2 Hz, 8 Hz), 7.00 (1H, d, J=8 Hz), 7.35 (2H, d, J=8 Hz), 7.60 (2H, d, J=8 Hz), 7.65 (2H, d, J=8 Hz), 7.95 (1H, br m), 8.05 (2H, d, J=8 Hz).

(c) 7-Methoxy-2-(4-(4-(6-methyl)-3-pyridyl)benzoylamino)butyl-1,2,3,4-tetrahydroisoquinoline Mass spectrum (API$^+$): Found: 430 (MH$^+$). $C_{27}H_{31} N_3 O_2$ requires 429

$^1$H NMR (CDCl$_3$) δ: 1.80 (4H, m), 2.55 (2H, m), 2.60 (3H, s), 2.75 (2H, t, J=6 Hz), 2.85 (2H, t, J=6 Hz), 3.50 (2H, m), 3.60 (2H, s), 3.70 (3H, s), 6.50 (1H, d, J=2 Hz), 6.70

(1H, dd, J=8 Hz, 2 Hz), 7.00 (1H, d, J=8 Hz), 7.25 (1H, m), 7.30 (2H, d, J=8 Hz), 7.70 (2H, d, J=8 Hz), 7.75 (1H, m), 7.85 (1H, m), 8.70 (1H, m).

EXAMPLE 6

2-(4-(4-(3-Cyanophenyl)benzoylamino)butyl-7-hydroxy-1,2,3,4-tetrahydroisoquinoline 2-(4-(4-(3-Cyanophenyl)benzoylamino)butyl-7-methoxy-1,2,3,4-tetrahydroisoquinoline (0.49 g, 1.14 mmol) in dichloromethane (3 ml) was treated with 1N hydrogen chloride in diethyl ether (3 ml) and the mixture evaporated in vacuo to afford the hydrochloride salt. The hydrochloride salt (054 g, 1.14 mmol) in dichloromethane (40 ml) was ice cooled as a solution of boron tribromide in dichloromethane (10 ml, 1M, 10 mmol) was added dropwise. After stirring at room temperature for 18 h. the mixture was added to ice and 0.880 ammonia (100 ml) and the mixture stirred for 1 h. then extracted into dichloromethane (2×100 ml). Combined organic extracts were washed with brine (50 mL) dried ($Na_2SO_4$) and evaporated in vacuo to afford a beige solid (0.43 g, 89%).

Mass spectrum ($API^+$): 426 ($MH^+$). $C_{27}H_{27}N_3O_2$ requires 425.

$^1$H NMR ($CDCl_3$) δ: 1.75 (4H, br m), 2.55 (2H, br m), 2.80 (4H, m), 3.40 (2H, s), 3.50 (2H, m), 6.35 (1H, d, J=2 Hz), 6.65 (1H, dd, J=2 Hz, 8 Hz), 6.85 (1H, d, J=8 Hz), 7.35 (2H, d, J=8 Hz), 7.55 (2H, t, J=8 Hz), 7.65 (2H, d, J=8 Hz), 7.80 (4H, m).

EXAMPLE 7

2-(4-(4-(3-Cyanophenyl)benzoylamino)butyl)-7-trifluoromethylsulfonyloxy-1,2,3,4-tetrahydroisoquinoline Trifluoromethanesulfonic anhydride (0.21 ml, 1.25 mmol) was added dropwise with stirring to an ice cooled solution of 2-(4-(4-(3-cyanophenyl)benzoylamino)butyl)-7-hydroxy-1,2,3,4-tetrahydroisoquinoline (0.41 g, 0.96 mmol) in anhydrous pyridine (5 ml). After stirring at room temperature for 18 h. the mixture was poured into 10% aqueous copper (II) sulphate (100 ml). The mixture was extracted with ethyl acetate (2×50 ml) and the combined extracts washed with 10% aqueous copper (II) sulfate (2×50 ml). water (50 ml), dried ($Na_2SO_4$) and evaporated in vacuo. The residue was chromatographed on silica gel using 10–100% ethyl acetate-hexane gradient elution to afford the title compound (0.263 g, 49%).

Mass spectrum $API^+$: 558 ($MH^+$). $C_{28}H_{26}F_3N_3O_4S$ requires 557.

$^1$H NMR ($CDCl_3$) δ: 1.75 (4H, br s), 2.60 (2H, m), 2.75 (2H, t, J=7 Hz), 2.90 (2H, t, J=7 Hz), 3.50 (2H, m), 3.65 (1H, s), 6.90 (1H, d, J=2 Hz), 7.00 (1H, dd, J=2 Hz, 8 Hz), 7.15 (3H, m), 7.45 (2H, d, J=8 Hz), 7.55 (1H, t, J=8 Hz), 7.65 (1H, m), 7.75 (3H, m), 7.85 (1H, m).

The following compounds were prepared in a similar manner to Example 7.

(a) 2-(4-(4-(4-Cyanophenyl)benzoylamino)butyl)-7-trifluoromethylsulfonyloxy-1,2,3,4-tetrahydroisoquinoline Mass spectrum ($API^+$): 558 ($MH^+$). $C_{28}H_{26}F_3N_3O_4S$ requires 557.

$^1$H NMR ($CDCl_3$) δ: 1.75 (4H, m), 2.60 (2H, m), 2.75 (2H, t, J=7 Hz), 2.90 (2H, t, J=7 Hz), 3.55 (2H, m), 3.65 (2H, s), 6.90 (1H, d, J=2 Hz), 7.05 (1H, dd, J=2 Hz, 8 Hz), 7.15 (2H, m), 7.50 (2H, d, J=8 Hz), 7.65 (2H, m), 7.75 (4H, m).

(b) 2-(4-(4-(4-Acetylphenyl)benzoylamino)butyl)-7-trifluoromethylsulfonyloxy-1,2,3,4-tetrahydroisoquinoline Mass spectrum $API^+$): 575 ($MH^+$). $C_{29}H_{29}F_3N_2O_5S$ requires 574.

$^1$H NMR ($CDCl_3$) δ: 1.75 (4H, m), 2.65 (5H, m), 2.80 (2H, t, J=7 Hz), 2.90 (2H, t, J=7 Hz), 3.55 (2H, m), 3.70 (2H, s), 6.90 (1H, d, J=2 Hz), 7.05 (1H, dd, J=2 Hz, 8 Hz), 7.10 (1H, m), 7.18 (1H, d, J=8 Hz), 7.55 (2H, d, J=8 Hz), 7.65 (2H, d, J=8 Hz), 7.75 (2H, d, J=8 Hz), 8.05 (2H, d, J=8 Hz).

EXAMPLE 8

2-(4-(4-(4-Methylsulfonylphenyl)benzoylamino) butyl)-7-trifluoromethylsulfonyloxy-1,2,3,4-tetrahydroisoquinoline Prepared from 2-(4-aminobutyl)-7-trifluoromethylsulfonyloxy-1,2,3,4-tetrahydroisoquinoline (0.15 g, 0.42 mmol) and 4-(4-methylsulfonylphenyl)benzoic acid (0.117 g, 0.42 mmol) using a procedure similar to that of Example 5 (0.15 g, 74%).

Mass spectrum ($API^+$): 611 ($MH^+$). $C_{28}H_{29}F_3N_2O_6S_2$ requires 610.

$^1$H NMR ($CDCl_3$) δ: 1.75 (4H, m), 2.60 (2H, m), 2.75 (2H, t, J=7 Hz), 2.90 (2H, t, J=7 Hz), 3.10 (3H, s), 3.50 (2H, m), 3.65 (2H, s), 6.90(1H, d, J=2 Hz), 7.00 (1H, dd, J=2 Hz, 8 Hz), 7.15 (1H, d, J=8 Hz), 7.20 (1H, m), 7.50 (2H, d, J=8 Hz), 7.75 (4H, m), 8.05 (2H, d, J=8 Hz).

The following compounds were prepared in a similar manner to Example 8

(a) 2-(4-(4-(3-Thienyl)benzoylamino)butyl)-7-trifluoromethylsulfonyloxy-1,2,3,4-tetrahydroisoquinoline Mass spectrum $API^+$): Found $MH^+$ 539. $C_{25}H_{25}N_2O_4S_2F_3$ requires 538.

$^1$H NMR ($CDCl_3$) δ: 1.72 (4H, m), 2.60 (2H, m), 2.70 (2H, m), 2.85, (2H, m), 3.50 (2H m), 3.63 (2H, s), 6.90–7.10 (3H, m), 7.12 (1H, d, J=8 Hz), 7.30–7.65 (5H, m), 7.69 (2H, d, J=7 Hz).

(b) 2-(4-(4-(3-Aminocarbonyl)phenyl)benzoylamino) butyl-7-trifluoromethylsulfonyloxy-1,2,3,4-tetrahydroisoquinoline Mass spectrum ($API^+$): Found $MH^+$ 576. $C_{28}H_{28}F_3N_3O_5S$ requires 575.

$^1$H NMR ($CDCl_3$) δ: 1.75 (4H, m), 2.60 (2H, m), 2.72 (2H, m), 2.85 (2H, m), 3.52 (2H, m), 3.62 (2H, m), 5.80 (1H, m), 6.3 (1H, m), 6.90 (1H, d, J=2 Hz), 7.00–7.20 (3H, m), 7.40–7.65 (3H, m), 7.70–7.90 (4H, m), 8.05 (1H, s)

(c) 2-(4-(4-(3-Acetylphenyl)benzoylamino)butyl)-7-trifluoromethylsulfonyloxy-1,2,3,4-tetrahydroisoquinoline Mass spectrum ($API^+$): Found 575 ($MH^+$). $C_{29}H_{29}F_3N_2O_5S$ requires 574.

$^1$H NMR ($CDCl_3$) δ: 1.75 (4H, m), 2.60 (2H, m), 2.65 (3H, s), 2.75 (2H, t, J=6 Hz), 2.90 (2H, t, J=9 Hz), 3.55 (2H, m), 3.65 (2H, s), 6.90 (1H, d, J=2 Hz), 6.95–7.10 (2H, m), 7.15 (1H, d, J=8 Hz), 7.55 (3H, m), 7.75 (3H, m), 7.95 (1H, dd, J=8 Hz, 2 Hz), 8.15 (1H, m).

(d) 2-(4-(4-(3-Methylsulfonylphenyl)benzoylamino) butyl)-7-trifluoromethylsulfonyloxy-1,2,3,4-tetrahydroisoquinoline Mass spectrum ($API^+$): Found 611 ($MH^+$). $C_{28}H_{29}F_3N_2O_6S_2$ requires 610.

$^1$H NMR ($CDCl_3$) δ: 1.75 (4H, m), 2.60 (2H, m), 2.75 (2H, t, J=6 Hz), 2.90 (2H, t, J=6 Hz), 3.10 (3H, s), 3.55 (2H, m), 3.65 (2H, s), 6.90 (1H, d, J=2 Hz), 7.05 (1H, dd, J=8 Hz,

2 Hz). 7.15 (1H, d, J=8 Hz), 7.20 (1H, m), 7.50 (2H, d, J=8 Hz), 7.70 (1H, m), 7.75 (2H, d, J=8 Hz), 7.85 (1 H, m), 7.95 (1H, m), 8.10 (1H, m).

(e) 2-(4-(4-(1-Methyl-4-pyrazolyl)benzoylamino)butyl)-7-trifluoromethylsulfonyloxy-1,2,3,4-tetrahydroisoquinoline Mass spectrum API$^+$): Found 537 (MH$^+$). $C_{25}H_{27}F_3N_4O_4S$ requires 536

$^1$H NMR (CDCl$_3$) δ: 1.75 (4H, m), 2.60 (2H, m), 2.75 (2H, t, J=6 Hz), 2.90 (2H, t, J=6 Hz), 3.50 (2H, m), 3.65 (2H, s), 3.95 (3H, s), 6.90 (1H, d, J=2 Hz), 7.05 (2H, m), 7.15 (1H, d, J=8 Hz), 7.35 (2H, d, J=8 Hz), 7.62 (1H, s), 7.65 (2H, d, J=8 Hz), 7.75 (1H, s).

(f) 2-(4-(4-(3-(5-Methyl-1,2,4-oxadiazolyl)benzoylamino)butyl)-7-trifluoromethylsulfonyloxy-1,2,3,4-tetrahydroisoquinoline Mass spectrum (API$^+$): Found 539 (MH$^+$). $C_{24}H_{25}F_3N_4O_5S$ requires 538.

$^1$H NMR (CDCl$_3$) δ: 1.75 (4H, m), 2.65 (2H, m), 2.70 (3H, s), 2.75 (2H, t, J=6 Hz), 2.90 (2H, t, J=6 Hz), 3.50 (2H, m), 3.60 (2H, s), 6.85 (1H, d, J=2 Hz), 7.00 (1H, dd, J=8 Hz, 2 Hz), 7.15 (1H, d, J=8 Hz), 7.25 (1H, m), 7.70 (2H, d, J=8 Hz), 7.95 (2H, d, J=8 Hz).

(g) 2-(4-(4-(2-Pyrimidyl)benzoylamino)butyl)-7-trifluoromethylsulfonyloxy-1,2,3,4-tetrahydroisoquinoline Mass spectrum API$^+$): Found 535 (MH$^+$). $C_{25}H_{25}F_3N_4O_4S$ requires 534.

$^1$H NMR (CDCl$_3$) δ: 1.80 (4H, m), 2.60 (2H, m), 2.75 (2H, t, J=6 Hz), 2.90 (2H, m, J=6 Hz), 3.55 (2H, m), 3.60 (2H, s), 6.95 (1H, d, J=2 Hz), 7.00 (1H, dd, J=8 Hz), 7.15 (1H, m), 7.17 (1H, m), 7.25 (1H, m), 7.75 (2H, d, J=8 Hz), 8.35 (2H, d, J=8 Hz), 8.85 (2H, d, J=5 Hz).

(h) 2-(4-(4-(4-(1-(2-Oxo)pyrrolidinyl)phenyl)benzoylamino)butyl)-7-trifluoromethylsulfonyloxy-1,2,3,4-tetrahydroisoquinoline Mass spectrum API$^+$). Found 616 (MH$^+$). $C_{31}H_{32}F_3N_4O_5S$ requires 615.

$^1$H NMR (CDCl$_3$) δ: 1.75 (4H, m), 2.20 (2H, m), 2.60 (4H, m), 2.75 (2H, t, J=6 Hz), 2.85 (2H, t, J=6 Hz), 3.50 (2H, m), 3.65 (2H, s), 3.90 (2H, t, J=7 Hz), 6.90 (1H, d, J=2 Hz), 7.05 (2H, m), 7.15 (1H, d, J=8 Hz), 7.50 (2H, d, J=8 Hz), 7.60 (2H, d, J=8 Hz), 7.75 (4H, m).

(i) 2-(4-(4-(4-Arminosulfonylphenyl)benzoylamino)butyl)-7-trifluoromethylsulfonyloxy-1,2,3,4-tetrahydroisoquinoline Mass spectrum (API$^+$): Found 612 (MH$^+$). $C_{27}H_{28}F_3N_3O_6S_2$ requires 611.

$^1$H NMR (CDCl$_3$) δ: 1.75 (4H, m), 2.60 (2H, m), 2.80 (2H, m), 2.95 (2H, m), 3.50 (2H, m), 3.65 (2H, s), 4.10 (2H, br s), 6.95 (1H, br s), 7.05 (1H, d, J=8 Hz), 7.20 (1H, d, J=8 Hz), 7.40 (1H, s), 7.60 (2H, d, J=8 Hz), 7.70 (2H, d, J=8 Hz), 7.85 (2H, d, J=8 Hz), 8.00 (2H, d, J=8 Hz).

(j) 2-(4-(4-(5-(1-Oxo)indanyl)benzoylamino)butyl)-7-trifluoromethylsulfonyloxy-1,2,3,4-tetrahydroisoquinoline Mass spectrum (API$^+$): Found 587 (MH$^+$). $C_{30}H_{29}F_3N_2O_5S$ requires 586.

$^1$H NMR (CDCl$_3$) δ: 1.75 (4H, m), 2.60 (2H, m), 2.75 (4H, m), 2.85 (2H, t, J=7 Hz), 3.20 (2H, t, J=6 Hz), 3.55 (2H, m), 3.65 (2H, s), 6.90 (1H, d, J=2 Hz), 7.00 (1H, dd, J=8 Hz, 2 Hz), 7.15 (2H, m), 7.50 (2H, d, J=8 Hz), 7.55 (1H, m), 7.65 (1H, s), 7.75 (2H, d, J=8 Hz), 7.80 (1H, d, J=8 Hz).

(k) 2-(4-(3-(6-(1-Pyrrolyl)pyridyl)carboxamido)butyl-7-trifluoromethylsulfonyloxy-1,2,3,4-tetrahydroisoquinoline Mass spectrum (API$^+$): Found MH$^+$ 523. $C_{24}H_{25}F_3N_4O_4S$ requires 522.

$^1$H NMR (CDCl$_3$) δ: 1.74 (5H, m), 2.58 (2H, m), 2.74 (2H, m), 2.85 (2H, m), 3.51 (2H, m), 3.64 (2H, s), 6.37 (2H, m), 6.96 (2H, m), 7.12 (2H, m), 7.50 (2H, m), 8.01 (1H, dd, J=8 Hz, 2 Hz), 8.65 (1H, d, J=2 Hz).

(l) 2-(4-(4-(3-(5-Methyl-1,2,4-oxadiazolyl)-phenylbenzoylamino)butyl)-7-trifluoromethylsulfonyloxy-1,2,3,4-tetrahydroisoquinoline Mass spectrum (API$^+$): Found 615 (MH$^+$). $C_{30}H_{29}F_3N_4O_5S$ requires 614.

$^1$H NMR (CDCl$_3$) δ: 1.76 (4H, m), 2.63 (2H, m), 2.68 (3H, s), 2.78 (2H, m), 2.90 (2H, m), 3.53 (2H, m), 3.67 (2H, s), 6.98 (3H, m), 7.15 (1H, d, J=7 Hz), 7.55 (2H, d, J=7 Hz), 7.68 (2H, d, J=7 Hz), 7.77 (2H, d, J=7 Hz), 8.15 (2H, d, J=7 Hz).

(m) 2-(4-(4-(2-(5-Methyl-1,3,4-oxadiazolyl)phenylbenzoylamino)butyl)-7-trifluoromethylsulfonyloxy-1,2,3,4-tetrahydroisoquinoline Mass spectrum (API$^+$): Found 615 (MH$^+$). $C_{30}H_{29}F_3N_4O_5S$ requires 614.

$^1$H NMR (CDCl$_3$) δ: 1.70–1.89 (4H, m), 2.61 (2H, t, J=5 Hz), 2.65 (3H, s), 2.75 (2H, t, J=5 Hz), 2.90 (2H, t, J=5 Hz), 3.52 (2H, m), 3.61 (2H, s), 6.91 (1H, d, J=4 Hz), 7.02 (1H, dd, J=4 and 10 Hz), 7.15 (2H, m), 7.52 (2H, d, J=7 Hz), 7.70 (2H, d, J=7 Hz). 7.79 (2H, d, J=7 Hz), 8.10 (2H, d, J=7 Hz).

(n) 2-(4-(4-(3-Methylaminocarbonyl)phenyl)benzoylamino)butyl-7-trifluoromethylsulfonyloxy-1,2,3,4-tetrahydroisoquinoline Mass spectrum (API$^+$): Found 590 (MH$^+$). $C_{29}H_{30}F_3N_3O_5S$ requires 589.

$^1$H NMR (CDCl$_3$) δ: 1.71–1.82 (4H, m), 2.59 (2H, t, J=5 Hz), 2.75 (2H, t J=5 Hz 2.89 (2H, t, J=5 Hz), 3.06 (3H, d, J=6 Hz), 3.51 (2H, q, J=5 Hz), 3.62 (2H, s), 6.75 (1H, m), 6.91 (1H, d, J=3 Hz), 7.00–7.10 (2H, m), 7.12 (1H, d, J=5 Hz), 7.49–7.56 (3H, m), 7.67–7.79 (4H, m), 7.98–8.00 (1H, m).

(o) 2-(4-(4-(4-Methylaminocarbonyl)phenyl)benzoylamino)butyl-7-trifluoromethylsulfonyloxy-1,2,3,4-tetrahydroisoquinoline Mass spectrum (API$^+$): Found 590 (MH$^+$). $C_{29}H_{30}F_3N_3O_5S$ requires 589.

$^1$H NMR (CDCl$_3$): 1.59–1.89 (4H, m), 2.60 (2H, t, J=4 Hz), 2.75, (2H, t, J=4 Hz), 2.88 (2H, t, J=4 Hz), 3.05 (3H, d, J=5 Hz), 3.45–3.60 (2H, m), 3.65 (2H, br s), 5.05–5.25 (1H, br s), 6.19–6.30 (1H, m), 6.90–7.15 (3H, m), 7.50 (2H, d, J=7 Hz), 7.61 (2H, d, J=7 Hz), 7.75 (2H, d, J=7 Hz), 7.85 (2H, d, J=7 Hz).

(p) 2-(4-(4-(4-Pyridyl)benzoylamino)butyl)-7-trifluoromethylsulfonyloxy-1,2,3,4-tetrahydroisoquinoline Mass spectrum (API$^+$): Found 534 (MH$^+$). $C_{26}H_{26}F_3N_3O_4S$ requires 533.

$^1$H NMR (CDCl$_3$) δ: 1.80 (4H, m), 2.60 (2H, m), 2.76 (2H, t, J=7 Hz), 2.88 (2H, t, J=7 Hz), 3.54 (2H, m), 3.65 (2H, s), 6.92 (1H, d, J=3 Hz), 7.02 (1H, dd, J=3,8 Hz), 7.15 (2H, m), 7.38–7.58 (4H, m), 7.78 (2H, d, J=10 Hz), 8.68 (2H, d, J=7 Hz).

(q) 2-(4-(4-(2-Thienyl)benzoylamino)butyl)-7-trifluoromethylsulfonyloxy-1,2,3,4-tetrahydroisoquinoline Mass spectrum (API$^+$): Found: 539 (MH$^+$). $C_{25}H_{25}F_3N_2O_5S_2$ requires 538.

$^1$H NMR (CDCl$_3$) δ: 1.75 (4H, m), 2.58 (2H, m), 2.72 (2H, t, J=7 Hz), 2.85 (2H, t, J=7 Hz), 3.50 (2H, m), 3.60 (2H, s), 6.94 (1H, d, J=3 Hz), 6.96–7.05 (4H, m), 7.34 (2H, m), 7.48 (2H, d, J=8 Hz), 7.66 (2H, d, J=8 Hz).

(r) 2-(4-(2-(5-(2-Pyridyl)thienylcarboxamido)butyl)-7-trifluoromethylsulfonyloxy-1,2,3,4-tetrahydroisoquinoline Mass spectrum (API$^+$): Found 540 (MH$^+$). $C_{24}H_{24}F_3N_3O_4S_2$ requires 539.

$^1$H NMR (CDCl$_3$) δ: 1.70 (4H, m), 2.58 (2H, m), 2.75 (2H, t, J=7 Hz), 2.80 (2H, t, J=7 Hz), 3.47 (2H, m), 3.65 (2H, s), 6.84 (1H, t), 6.94 (1H, d, J=3 Hz), 7.02 (1H, dd, J=3, 10 Hz), 7.08–7.25 (2H, m), 7.47 (2H, m), 7.58–7.78 (2H, m), 8.60 (1H, d, J=7 Hz).

(s) 2-(4-(4-(4-Acetylphenyl)benzoylamino)butyl)-7-trifluoroethoxy-1,2,3,4-tetrahydroisoquinoline Mass spectrum (API$^+$): Found 511 (MH$^+$). $C_{29}H_{30}F_3N_2O_3$ requires 510.

$^1$H NMR (CDCl$_3$) δ: 1.78 (4H, m), 2.60 (2H, m), 2.65 (3H, s), 2.75 (2H, m), 2.87 (2H, m), 3.53 (2 H, m), 3.62 (2H, s), 6.87 (1H, br s), 6.99 (1H, m), 7.09 (1H, d, J=8 Hz), 7.32 (1H, m), 7.46 (2H, d, J=8 Hz), 7.65 (2H, d, J=8 Hz), 7.74 (2H, d, J=8 Hz), 8.04 (2H, d, J=8 Hz).

(t) 2-(4-(4-(4-Acetylphenyl)benzoylamino)butyl)-7-trifluoromethyl-1,2,3,4-tetrahydroisoquinoline Mass spectrum (API$^+$): Found 495 (MH$^+$). $C_{29}H_{29}F_3N_2O_2$ requires 494.

$^1$H NMR (CDCl$_3$) δ: 1.79 (4H, m), 2.62 (2 H, m), 2.65 (3H, s), 2.76 (2H, m), 2.93 (2H, m), 3.53 (2H, m), 3.68 (2H, s), 7.18 (1H, d, J=8 Hz), 7.27 (1H, d, J=4 Hz), 7.36 (1H, d, J=8 Hz), 7.42 (2H, d, J=8 Hz), 7.62 (2H, d, J=8 Hz), 7.88 (2H, d, J=8 Hz), 8.02 (1H, br s), 8.03 (2H, d, J=8 Hz).

EXAMPLE 9

2-(4-(4-Phenylbenzoylamino)butyl)-7-(2-thienyl)sulfonyloxy-1,2,4-tetrahydroisoquinoline A solution of 7-hydroxy-2-(4-(4-phenylbenzoylamino)butyl)-1,2,4-tetrahydroisoquinoline (0.5 g, 1.3 mmol), thiophene-2-sulfonyl chloride (0.27 g, 1.5 mmol) and triethylamine (0.21 ml, 1.5 mmol) in dichloromethane (20 ml) was stirred at room temperature for 18 h. The reaction mixture was poured onto saturated aqueous potassium carbonate (25 ml) and extracted into dichloromethane (3×20 ml). The combined extracts were washed with brine, dried (Na$_2$SO$_4$) and evaporated in vacuo. Chromatography on silica using 10–100% ethyl acetate-pentane gradient elution gave the title compound as a yellow solid (226 mg, 32%).

Mass spectrum (API$^+$): 547 (MH$^+$). $C_{30}H_{30}N_2O_4S_2$ requires 546.

$^1$H NMR (CDCl$_3$) δ: 1.71 (4H, m), 2.54 (2H, m), 2.69 (2H, m), 2.82 (2H, m), 3.30–3.60 (4H, m), 6.60–6.85 (2H, m), 6.90–7.17 (4H, m), 7.30–7.78 (10H, m).

The following compound was prepared in a similar manner to Example 9.

(a) 7-(4-(3,5-Dimethyl)isoxazolyl)sulfonyloxy-2-(4-(4-phenylbenzoylamino)butyl)-1,2,3,4-tetrahydroisoquinoline Mass spectrum (API$^+$): 560 (MH$^+$). $C_{31}H_{33}N_3O_5S$ requires 559.

$^1$H NMR (CDCl$_3$) δ: 1.71 (4H, m), 2.32 (3H, s), 2.39 (3H, s), 2.54 (2H, m), 2.69 (2H, m), 2.84 (2H, m), 3.38–3.65 (4H, m), 6.65–6.85 (2H, m), 6.95–7.20 (2H, m), 7.30–7.60 (7H, m), 7.75 (2H, d, J=8 Hz).

EXAMPLE 10

7-Acetyl-2-(4-(4-phenylbenzoylamino)butyl)-1,2,3,4-tetrahydroisoquinoline 2-(4-(4-Phenylbenzoylamino)butyl)-7-trifluoromethylsulfonyloxy-1,2,3,4-tetrahydroisoquinoline (0.515 g, 0.97 mmol), (1-ethoxyvinyl)tributyltin (0.420 g, 1.16 mmol), lithium chloride (0.121 g, 2.85 mmol) and tetrakis-(triphenylphosphine)palladium (0) (0.057 g, 0.05 mmol) in 1,4-dioxane (15 ml) were heated at reflux under argon for 16 h. The cooled reaction mixture was treated with water (2.0 ml) and aqueous 5N hydrogen chloride (4 drops), then stirred at room temperature for 0.5 h. The resulting solution was poured onto saturated, aqueous potassium carbonate (20 ml) and the product was extracted with ethyl acetate (2×25 ml). The combined organic extracts were washed with brine (40 ml), dried (Na$_2$SO$_4$) and evaporated in vacuo. The residue was chromatographed on silica using 50–100% ethyl acetate—pentane gradient elution to afford the title compound as a colourless solid (0.210 g, 51%).

Mass spectrum (API$^+$): 427 (MH$^+$). $C_{28}H_{30}N_2O_2$ requires 426.

$^1$H NMR (CDCl$_3$) δ: 1.78 (4H, br m), 2.45 (3H, s), 2.61 (2H, m), 2.75 (2H, t, J=8 Hz), 2.92 (2H, t, J=8 Hz), 3.52 (2H, m), 3.66 (2H, s), 7.15 (2H, d, J=8 Hz), 7.30–7.50 (11H, br m).

EXAMPLE 11

2-(4-(4-Phenylbenzoylamino)butyl)-7-(3-pyridyl)sulfonyloxy-1,2,3,4-tetrahydroisoquinoline To a stored solution of 7-hydroxy-N-(4-(4-phenylbenzoylamino)butyl)-1,2,3,4-tetrahydroisoquinoline (05 g, 1.3 mmol) and triethylamine (0.21 ml; 1.5 mmol) in dichloromethane (20 ml) was added pyridine-3-sulfonyl chloride (0.25 g, 1.4 mmol). The mixture was stirred for 18 h, then partitioned between dichloromethane (4×30 ml) and saturated aqueous NaHCO$_3$ (100 ml). Combined organic extracts were dried (Na$_2$SO$_4$) and evaporated in vacuo to give an oil. Chromatography on silica using 0–5% methanolethyl acetate gradient elution gave the title compound (0.06 g, 12%) as an oil.

$^1$H NMR(CDCl$_3$) δ: 1.62–1.87 (4H, m), 2.55–2.70 (2H, m), 2.72–2.92 (4H, m), 3.41–3.60 (2H, m), 3.65 (2H, s), 6.68–6.78 (2H, m), 7.00 (1H, d, J=10 Hz), 7.20 (1H, t, J=4 Hz), 7.31–7.65 (8H, m), 7.78 (2H, d, J=10 Hz), 8.05–8.15 (1H, m), 8.88 (1H, dd, J=2 and 4 Hz), 9.00 (1H, d, J=2 Hz).

The following compounds were prepared in a similar manner to Example 11

(a) 2-(4-(4-Phenylbenzoylamino)butyl)-7-(2-cyanophenyl)sulfonyloxy-1,2,3,4-tetrahydroisoquinoline Mass spectrum (API$^+$): Found 566 (MH$^+$). $C_{33}H_{31}N_3O_4S$ requires 565.

$^1$H NMR (CDCl$_3$) δ: 1.64–1.80 (4H, m), 2.53 (2H, t, J=5 Hz), 2.70 (2H, t, J=5 Hz), 2.82 (2H, t, J=5 Hz), 3.49–3.60 (4H, m), 6.89–6.92 (2H, m), 7.00 (1H, d, J=6 Hz), 7.12 (1H, t, J=6 Hz), 7.32–7.60 (7H, m), 7.71–7.80 (4H, m), 7.92 (1H, dd, 2 and 6 Hz), 8.03 (1H, dd, J=2 and 6 Hz).

(b) 2-(4(4-(Phenylbenzoylamino)butyl)-7-(3cyanophenyl)sulfonyloxy-1,2,3,4-tetrhydroisoquinoline Mass spectrum (API$^+$) Found 566 (MH$^+$) $C_{30}H_{31}N_3O_4S$ requires 565.

$^1$H NMR (CDCl$_3$) δ: 1.55–1.70 (4H, m), 2.55 (2H, t, J=6 Hz), 2.70 (2H, t, J=6 Hz), 2.85 (2H, t, J=6 Hz), 3.49–3.58 (4H, m), 6.62–6.72 (2H, m), 7.00 (1H, d, J=7 Hz), 7.10 (1H, t, J=6 Hz), 7.35–7.80 (10H, m), 7.89–8.10 (3H, m).

(c) 2-(4(4-Phenylbenzoylamino)butyl)-7-thienyl)sulfonyloxy-1,2,3,4-tetrahydroisoquinoline Mass spectrum (API$^+$): Found: 547 (MH$^+$) $C_{30}H_{30}N_2O_4S_2$ requires 546.

¹H NMR (CDCl₃) δ: 1.61–1.87 (4H, m), 2.52 (2H, t, J=5 Hz), 2.70 (2H, t, J=5 Hz), 2.83 (2H, t, J=5 Hz), 3.42 –3.58 (4H, m), 6.70 (2H, m), 7.00 (2H, d, J=6 Hz), 7.31–7.55 (8H, m), 7.57 (2H, d, J=6 Hz), 7.72 (1H, d, J=6 Hz), 7.90 (1H, m).

EXAMPLE 12

7-Methoxycarbonylmethyl-2-(4-(4-phenylbenzoylamino)butyl)-1,2,3,4-tetrahydroisoquinoline A mixture of thallium (III) nitrate trihydrate (0.73 g, 1.6 mmol), K10 clay (1.65 g) and trimethyl orthoformate (1.8 ml, 1.6 mmol) in methanol (3 ml) was stirred at room temperature for 15 min. The solvent was evaporated in vacuo and dichloromethane (5 ml) was added to the residue. To this mixture was added a solution of 7-acetyl-2-(4-(4-phenylbenzoylamino)butyl)-1,2,3,4-tetrahydroisoquinoline, hydrochloride (0.50 g, 1.1 mmol) in dichloromethane (15 ml) and the reaction mixture was stirred for 4 h. The suspended solid was removed by filtration and the filtrate was washed with saturated aqueous potassium carbonate (2×30 ml), then brine (30 ml). Drying (Na₂SO₄) and evaporation in vacuo afforded a yellow gum which was chromatographed on silica using 20–100% ethyl acetate—pentane gradient elution to afford the title compound as an off-white solid (0.15 g, 30%).

Mass spectrum (API⁺): Found 457 (MH⁺). C₂₉H₃₂N₂O₃ requires 456.

¹H NMR (CDCl₃) δ: 1.75 (4H, m), 2.58 (2H, m), 2.74 (2H, t, J=7 Hz), 2.86 (2H, t, J=7 Hz), 3.52 (4H, m), 3.60 (2H, s), 3.65 (3H, s), 6.90 (1H, s), 7.04 (2H, s), 7.30–7.60 (8H, m), 7.72 (2H, d, J=8 Hz).

EXAMPLE 13

7-Ethoxycarbonylmethyl-2-(4-(4-phenylbenzoylamino)butyl)-1,2,3,4-tetrahydroisoquinoline A stirred, ice-cooled solution of 7-methoxycarbonylmethyl-2-(4-(4-phenylbenzoylamino)butyl)-1,2,3,4-tetrahydroisoquinoline (0.202 g, 0.46 mmol) in ethanol (10 ml) was treated with concentrated sulfuric acid (0.53 ml, 0.53 mmol). The mixture was heated at reflux for 2 h. The solvent was evaporated in vacuo and the residue was dissolved in ethyl acetate (30 ml) and saturated aqueous sodium bicarbonate solution (30 ml). The organic phase was separated and washed with brine. Drying (Na₂SO₄) and evaporation in vacuo afforded an orange oil which was chromatographed on silica using 50–100% ethyl acetate-pentane gradient elution to afford the title compound as a colourless oil (120 mg, 56%).

Mass spectrum (API⁺): Found 471 (MH⁺). C₃₀H₃₄N₂O₃ requires 470.

¹H NMR (CDCl₃) δ: 1.24 (3H, t, J=8 Hz), 1.75 (4H, m), 2.56 (2H, m), 2.74 (2H, t, J=6 Hz), 2.84 (2H, t, J=6 Hz), 3.50 (4H, m), 3.62 (2H, s), 4.10 (2H, q, J=8 Hz), 6.92 (1H, s), 7.05 (2H, s), 7.30–7.62 (8H, m), 7.70 (2H, d, J=11 Hz).

EXAMPLE 14

7-(2-Cyanophenoxy)-2-(4-(4-phenylbenzoylamino) butyl-1,2,3,4-tetrahydroisoquinoline A stirred mixture of 7-hydroxy-2-(4-(4phenylbenzoylamino)butyl)-1,2,3,4-tetrhydroisoquinoline (0.605 g, 1.51 mmol), 2-fluorobenzonitrile (0.182 g, 1.51 mmol) and potassium carbonate (0.518 g, 3.75 mmol) in dimethylformamide (8 ml) was heated at 120° C. for 16 h. The cooled reaction mixture was partitioned between ethyl acetate (30 ml) and water (20 ml). The organic phase was separated and washed with water (4×20 ml) then brine (20 ml). Drying (Na₂SO₄) and evaporation in vacuo afforded an oil which was chromatographed on silica using 20–100% ethyl acetate-pentane gradient elution. The title compound was afforded as a pale yellow oil (0.400 g, 53%).

Mass spectrum (API⁺): Found 502 (MH⁺). C₃₃H₃₁N₃O₂ requires 501.

¹H NMR (CDCl₃) δ: 1.78 (4H, m), 2.56 (2H, m), 2.76 (2H, t, J=7 Hz), 2.88 (2H, t, J=7 Hz), 3.52 (2H, m), 3.60 (2H, s), 6.75 (2H, m), 6.85 (1H, dd, J=3, 8 Hz), 7.02 (3H, m), 7.30–7.68 (9H, m), 7.75 (2H, d, J=10 Hz).

EXAMPLE 15

7-Bromo-2-(4-(4-phenylbenzoylamino)butyl)-1,2,3,4-tetrahydroisoquinoline

7-Bromo-2-tufluoroacetyl-1,2,3,4-tetrahydroisoquinoline (7.20 g, 23 mmol) and potassium carbonate (16.8 g, 122 mmol) in 10% aqueous methanol (250 ml) were heated at reflux, with stirring, for 2 h. After cooling the solvents were removed in vacuo and the residue was partitioned between water (200 ml) and dichloromethanc (100 ml). The aqueous layer was extracted further with dichloromethane (2×50 ml). The combined organics were washed with brine, dried Na₂SO₄) and evaporated in vacuo to afford 7-bromo1,2,3,4-tetrahydroisoquinoline as a brown oil (4.50 g, 21 mmol, 92%). The oil was stirred with 4-(4-phenylbenzoylaminobutyraidehyde (5.71 g, 21 mmol) in dichloromethane (250 ml) and sodium triacetoxyborohydride (6.71 g, 32 mmol) was added. After stirring for 16 h at room temperature the mixture was diluted with dichloromethane (100 ml) then washed with brine (100 ml). Drying (Na₂SO₄) and evaporation of the solvent in vacuo gave a solid which was chromatographed on silica using 20–100% ethyl acetate-pentane gradient elution to afford the title compound as a white solid (6.68 g, 68%).

Mass spectrum (API⁺): Found 463, 465 (MH⁺). C₂₆H₂₇BrN₂O requires 462, 464.

EXAMPLE 16

7-Cyano-2-(4-(4-phenylbenzoylamino)butyl)-1,2,3,4-tetrahydroisoquinoline

A mixture of 7-Bromo-2-(4-(4-phenylbenzoylamino) butyl)-1,2,3,4-tetrahydroisoquinoline (3.84 g, 8.3 mmol) and copper (I) cyanide (1.04 g, 11.4 mmol) in N-methyl-2-pyrrolidinone (20 ml) was heated at reflux for 1.5 h. The cooled mixture was poured onto 0.880 ammonia (50 ml) and crushed ice (~50 g) with stirring. The product was extracted into ethyl acetate (100 ml) and washed further with 0.880 ammonia (2×30 ml), then brine. Drying (Na₂SO₄) and evaporation of the solvent in vacuo afforded a brown oil. Chromatography on silica using 20–100% ethyl acetate-pentane gradient elution afforded the title compound as a colourless gum (1.58 g, 47%).

¹H NMR (CDCl₃) δ: 1.75 (4H, m), 2.60 (2H, m), 2.74 (2H, t, J=7 Hz), 2.92 (2H, t, J=7 Hz), 3.50 (2H, m), 3.62 (2H, s), 7.05 (1H, t), 7.16 (1H, d, J=10 Hz), 7.26–7.52 (9H, m), 7.74 (2H, d, J=10 Hz).

We claim:
1. A compound of formula (I):

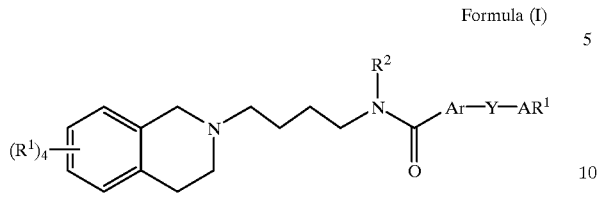

Formula (I)

wherein:
R¹ represents a substituent selected from: a hydrogen or halogen atom; a hydroxy, cyano, nitro, trifluoromethyl, trifluoromethoxy, trifluoromethanesulfonyloxy, $C_{1-4}$alkyl, $C_{1-4}$alkoxy, aryl$C_{1-4}$alkoxy, $C_{1-4}$alkylthio, $C_{1-4}$alkoxy$C_{1-4}$akyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy, arylsulphonyl$C_{1-4}$alkyl, $C_{1-4}$alkylsulphonamido, $C_{1-4}$alkylamido, $C_{1-4}$alkylsulphonamido$C_{1-4}$alkyl, $C_{1-4}$alkyamido$C_{1-4}$alkyl, arylsulphonamido, arylcarboxamido, arylsulphonarnido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH_2)_p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacyloalkane or $C_{3-6}$(2-oxo) azacycloalkane ring and p represents zero or an integer from 1 to 4; or a group $Ar^2$—Z, wherein $Ar^2$ represents an optionally substituted phenyl ring or an optionally substituted 5- or 6-membered aromatic heterocyclic ring and Z represents a bond, O, S, or $CH_2$;

R² represents a hydrogen atom or a $C_{1-4}$alkyl group;
q is 1 or 2;
Ar and Ar¹ each independently represent an optionally substituted phenyl ring or an optionally substituted 5- or 6-membered aromatic heterocyclic ring; and
Y represents a bond, —NHCO—, —CONH—, —CH₂—, or —(CH₂)$_m$Y¹(CH₂)$_n$—, wherein Y¹ represents O, S, SO₂, or CO and m and n each represent zero or 1 such that the sum of m+n is zero or 1;
or a salt thereof.

2. A compound according to claim 1 wherein q represents 1.

3. A compound as claimed in claim 1 wherein Y represents a bond.

4. A compound as claimed in claim 1 wherein Ar represents unsubstituted phenyl.

5. A compound of formula (I) which is:
7-Methoxy-N-(4-(4-phenylbenzoylamino)butyl)-1,2,3,4-tetrahydroisoquinoline;
7-Hydroxy-N-4-(4-phenylbenzoylamino)butyl)-1,2,3,4-tetrahydroisoquinoline;
2-(4-(4-Cyanophenyl)benzoylamino)butyl)-7-hydroxy-1,2,3,4-tetrahydroisoquinoline 2-(4-(4-(4-Acetylphenyl)benzoylamino)butyl)-7-hydroxy-1,2,3,4-tetrahydroisoquinoline N-(4-(4-Phenylbenzoylamino)butyl)-7-trifluoromethylsulfonyloxy-1,2,3,4-tetrahydroisoquinoline;
7-Methylsulfonyloxy-N-(4-(4-phenylbenzoylamino)butyl)-1,2,3,4-tetrahydroisoquimoline;
2-(4-(4-(3-Cyanophenyl)benzoylamino)butyl)-7-methoxy-1,2,3,4-tetrahydroisoquinoline;
2-(4-(4-(4-Cyanophenyl)benzoylamino)butyl)-7-methoxy-1,2,3,4-tetrahydroisoquinoline;
2-(4-(4-(4-Acetylphenyl)benzoylamino)butyl)-7-methoxy-1,2,3,4-terrahydroisoquinoline;
2-(4-(4-(3-Cyanophenyl)benzoylamino)butyl)-7-hydroxy-1,2,3,4-tetrahydroisoquinoline;
2-(4-(4-(3-Cyanophenyl)benzoylamino)butyl)-7-trifluoromethydsulfonyloxy-1,2,3,4-tetrahydroisoquinoline;
2-(4-(4-(4-Cyanophenyl)benzoylamino)butyl)-7-trifluoromethylsulfonyloxy-1,2,3,4-tetrahydroisoquinoline;
2-(4-(4-(4-Acetylphenyl)benzoylamino)butyl)-7-trifluoromethylsulfonyloxy-1,2,3,4-tetrahydroisoquinoline;
2-(4-(4-(4-Methylsulfonylphenyl)benzoylamino)butyl)-7-trifluoromethylsulfonyloxy-1,2,3,4-tetrahydroisoquinoline;
2-(4-(4-Phenylbenzoylamino)butyl)-7-(2-thienyl)sulfonyloxy-1,2,3,4-tetrahydroisoquinoline;
7-(4-(3,5-Dimethyl)isoxazolyl)sulfonyloxy-2-(4-(4-phenylbenzoylamino)butyl)-1,2,3,4-tetrahydroisoquinoline;
7-Acetyl-2-(4-(4-phenylbenzoylamino)butyl)-1,2,3,4-tetrahydroisoquinoline;
7-Methoxy-2-(4-(4-(6-methyl)-3-pyridyl)benzoylamino)butyl-1,2,3,4-tetrahydroisoquinoline;
2-(4-(4-(3-Thienyl)benzoylamino)butyl)-7-trifluoromethylsulfonyloxy-1,2,3,4-tetrahydroisoquinoline;
2-(4-(4-(3-Aminocarbonyl)phenyl)benzoylamino)butyl-7-trifluoromethylsulfonyloxy-1,2,3,4-tetrahydroisoquinoline;
2-(4-(4-(3-Acetylphenyl)benzoylamino)butyl)-7-trifluoromethylsulfonyloxy-1,2,3,4-tetrahydoisoquinoline;
2-(4-(4-(3-Methylsulfonylphenyl)benzoylamino)butyl)-7-trifluoromethylsulfonyloxy-1,2,3,4-tetrahydroisoquinoline;
2-(4-(4-(1-Methyl-4-pyrazolyl)benzoylamino)butyl)-7-trifluoromethylsulfonyloxy-1,2,3,4-tetrahydroisoquinoline;
2-(4-(4(-(5-Methyl-1,2,4-oxadiazolyl)benzoylamino)butyl)-7-triuoromethylsulfonyloxy-1,2,3,4-tetrahydroisoquinoline;
2-(4-(4-(2-Pyrimidyl)benzoylamino)butyl)-7-trifluoromethylsulfonyloxy-1,2,3,4-tetrahydroisoquinoline;
2-(4-(4-(4-(1-(2-Oxo)pyrrolidinyl)phenyl)benzoylamino)butyl)-7-trifluoromethylsulfonyloxy-1,2,3,4-tetrahydroisoquinoline;
2-(4-(4-(4-Aminosulfonylphenyl)benzoylamino)butyl)-7-trifluoromethylsulfonyloxy-1,2,3,4-tetrahydroisoquinoline;
2-(4-(4-(5-(1-Oxo)indanyl)benzoylamino)butyl)-7-trifluoromethylsulfonyloxy-1,2,3,4-tetrahydroisoquinoline;
2-(4-(3-(6-(1-Pyrrolyl)pyridyl)carboxamido)butyl-7-trifluoromethylsulfonyloxy-1,2,3,4-tetrahydroisoquinoline;
2-(4-(4-(3-(5-Methyl-1,2,4-oxadiazolyl)-phenylbenzoylamino)butyl)-7- trifluoromethylsulfonyloxy-1,2,3,4-tetrahydroisoquinoline;

2-(4-(4-(2-(5-Methyl-1,3,4-oxadiazolyl)phenylbenzoylamino)butyl)-7-trifluoromethylsulfonyloxy-1,2,3,4-tetrahydroisoquinoline;

2-(4-(4-(3-Methylaminocarbonyl)phenyl)benzoylamino)butyl-7-trifluoromethylsulfonyloxy-1,2,3,4-tetrahydroisoquinoline;

2-(4-(4-(4-Methylaminocarbonyl)phenyl)benzoylamino)butyl-7-trifluoromethylsulfonyloxy-1,2,3,4-tetrahydroisoquinoline;

2-(4-(4-(4-Pyridyl)benzoylamino)butyl)-7-trifluoromethylsulfonyloxy-1,2,3,4-tetrahydroisoquinoline;

2-(4-(4-(2-Thienyl)benzoylamino)butyl)-7-trifluoromethylsulfonyloxy-1,2,3,4-tetrahydroisoquinoline;

2-(4-(2-(5-(2-Pyridyl)thienylcarboxamido)butyl)-7-trifluoromethylsulfonyloxy-1,2,3,4-tetrahydroisoquinoline;

2-(4-(4-Phenylbenzoylamino)butyl)-7-(3-pyridyl)sulfonyloxy-1,2,3,4-tetrahydroisoquinoline;

2-(4-(4-Phenylbenzoylamino)butyl)-7-(2-cyanophenyl)sulfonyloxy-1,2,3,4-tetrahydroisoquinoline;

2-(4-(4-(Phenylbenzoylamino)butyl)-7-(3-cyanophenyl)sulfonyloxy-1,2,3,4-tetrahydroisoquinoline;

2-(4-(4-Phenylbenzoylamino)butyl)-7-(3-thienyl)sulfonyloxy-1,2,3,4-tetrahydroisoquinoline;

7-Methoxycarbonylmethyl-2-(4-(4-phenylbenzoylamino)butyl)-1,2,3,4-tetrahydroisoquinoline;

7-Ethoxycarbonylmethyl-2-(4-(4-phenylbenzoylamino)butyl)-1,2,3,4-tetrahydroisoquinoline;

7-(2-Cyanophenoxy)-2-(4-(4-phenylbenzoylamino)butyl-1,2,3,4-tetrahydroisoquinoline;

7-Bromo-2-(4-(4-phenylbenzoylamino)butyl)-1,2,3,4-tetrahydroisoquinoline;

7-Cyano-2-(4-(4-phenylbenzoylamino)butyl)-1,2,3,4-tetrahydroisoquinoline;

2-(4-(4-(4-Acetylphenyl)benzoylamino)butyl)-7-trifluoromethoxy-1,2,3,4-tetrahydroisoquinoline;

2-(4-(4-(4-Acetylphenyl)benzoylamino)butyl)-7-trifluommethyl-1,2,3,4-tetrahydroisoquinoline;

or a salt thereof.

6. A process for preparing a compound of formula (I) as defined in claim 1 which process comprises:

(a) reacting a compound of formula (II):

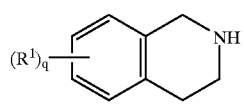

Formula (II)

wherein $R^1$ and q are as defined in claim 1;

with a compound of formula (III):

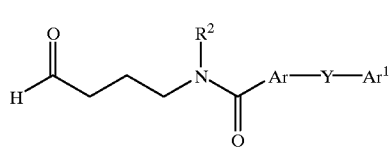

Formula (III)

wherein $R^2$, Y, Ar and $Ar^1$ are as defined in claim 1;

(b) reacting a compound of formula (IV):

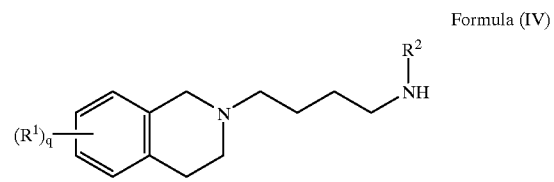

Formula (IV)

wherein $R^1$ and $R^2$ are as defined in claim 1;
with a compound of formula (V):

$Ar^1$—Y—ArCOX     Formula (V)

wherein Y, Ar and $Ar^1$ are as defined in claim 1 and X is a halogen atom or the residue of an activated ester;

(c) preparing a compound of formula (I) wherein $R^1$ is $Ar^2$—Z and Z is a bond, reacting a compound of formula (VI):

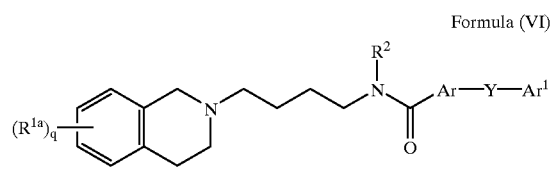

Formula (VI)

wherein one $R^{1a}$ represents a group W wherein W is a halogen atom or a trifluoromethylsulphonyloxy group, or W is a group M selected from a boron compound or a metal function, and when q is 2 the other $R^{1a}$ is $R^1$; with a compound $Ar^2$—$W^1$, wherein $W^1$ is a halogen atom or a trifluoromethylsulphonyloxy group when W is a group M or $W^1$ is a group M when W is a halogen atom or a trifluoromethylsulphonyloxy group;

(d) preparing a compound of formula (I) wherein $R^1$ is $Ar^2$—Z and Z is O or S, reacting a compound of formula (VII):

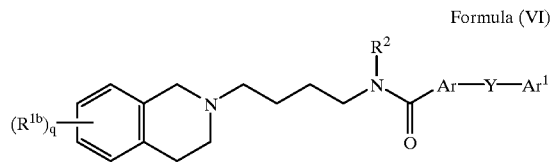

Formula (VI)

wherein one $R^{1b}$ represent a group ZH and when q is 2 the other $R^{1b}$ represents $R^1$; with a reagent serving to introduce the group $Ar^2$;

(e) preparing a compound of formula (I) where Y is a bond, reaction of a compound of formula (VIII):

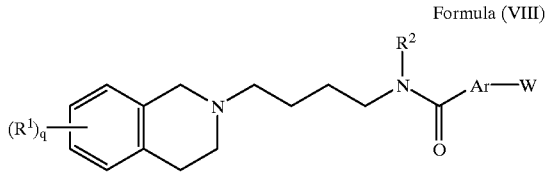

Formula (VIII)

wherein R¹, R², Ar and W are as defined in claim 1, with a compound Ar¹—W¹, wherein W¹ is a halogen atom or a trifluoromethylsulphonyloxy group when W is a group M, or W¹ is a group M when W is a halogen atom or a trifluoromethylsulphonyloxy group;

(f) interconverting one compound of formula (I) to a different compound of formula (I); and optionally thereafter forming a salt of formula (I).

7. A pharmaceutical composition comprising a compound of formula (I) as claimed in claim 1 or a physiologically acceptable salt thereof and a physiologically acceptable carrier therefor.

8. A method of treating a condition which requires modulation of a dopamine receptor which comprises administering to a subject in need thereof an effective amount of a compound of formula (I) as claimed in claim 1 or a physiologically acceptable salt thereof.

9. The method according to claim 8 wherein the dopamine receptor is a dopamine $D_3$ receptor.

10. The method according to claim 8 wherein a dopamine antagonist is required.

11. The method according to claim 8 wherein the condition is a psychotic condition.

* * * * *

UNITED STATES PATENT AND TRADEMARK OFFICE
CERTIFICATE OF CORRECTION

PATENT NO : 6,046,210
DATED : April 4, 2000
INVENTOR(S) : Stemp et al.

It is certified that errors appear in the above-identified patent and that said Letters Patent are hereby corrected as shown below:

On the first page under "Abstract", Formula I, please change "$(R^1)_4$" to read "$(R^1)_q$".

On the first page under "Abstract", Formula I, please change "$AR^1$" to read "$Ar^1$".

In claim 1, Formula I, please change "$(R^1)_4$" to read "$(R^1)_q$".

In claim 1, Formula I, please change "$AR^1$" to read "$Ar^1$".

In claim 1, line 25, after "arylcarboxamido", please correct "arylsulphonamido$C_{1-4}$alkyl" to read "arylsulphonamido$C_{1-4}$alkyl".

Signed and Sealed this

Eighth Day of May, 2001

Attest:

NICHOLAS P. GODICI

*Attesting Officer*     *Acting Director of the United States Patent and Trademark Office*